US010475593B2

United States Patent
Sagaidak et al.

(10) Patent No.: US 10,475,593 B2
(45) Date of Patent: Nov. 12, 2019

(54) USE OF HALOGEN DERIVATIVES OF HISTIDINE AS ELECTROLYTIC SALT IN A PHOTOVOLTAIC DYE CELL

(71) Applicants: CENTRE NATIONAL DE LA RECHERCHE SCIENTIFIQUE, Paris (FR); UNIVERSITE DE PICARDIE JULES VERNE, Amiens (FR)

(72) Inventors: Iryna Sagaidak, Amiens (FR); Miguel Flasque, Amiens (FR); Frédéric Sauvage, Digeon (FR); Albert Nguyen Van Nhien, Amiens (FR)

(73) Assignees: CENTRE NATIONAL DE LA RECHERCHE SCIENTIFIQUE, Paris (FR); UNIVERSITE DE PICARDIE JULES VERNE, Amiens (FR)

( * ) Notice: Subject to any disclaimer, the term of this patent is extended or adjusted under 35 U.S.C. 154(b) by 162 days.

(21) Appl. No.: 15/523,867

(22) PCT Filed: Nov. 4, 2015

(86) PCT No.: PCT/FR2015/052984
§ 371 (c)(1),
(2) Date: May 2, 2017

(87) PCT Pub. No.: WO2016/071637
PCT Pub. Date: May 12, 2016

(65) Prior Publication Data
US 2017/0323732 A1    Nov. 9, 2017

(30) Foreign Application Priority Data
Nov. 5, 2014 (FR) ..................... 14 60661

(51) Int. Cl.
*H01L 31/00* (2006.01)
*H01G 9/20* (2006.01)
*C07D 233/64* (2006.01)

(52) U.S. Cl.
CPC ......... *H01G 9/2013* (2013.01); *C07D 233/64* (2013.01); *H01G 9/2022* (2013.01);
(Continued)

(58) Field of Classification Search
CPC ........................... H01G 9/2013; C07D 233/64
See application file for complete search history.

(56) References Cited

U.S. PATENT DOCUMENTS

2011/0274638 A1   11/2011   Bouix-Peter et al.

FOREIGN PATENT DOCUMENTS

WO    2004038745    5/2004

OTHER PUBLICATIONS

List of SciFinder results for chemical structure search (Year: 2018).*
(Continued)

*Primary Examiner* — Angelo Trivisonno
(74) *Attorney, Agent, or Firm* — Troutman Sanders LLP

(57) ABSTRACT

The invention relates to the use of halogenated histidine derivatives as electrolyte salts in the preparation of an electrolyte composition in a photoelectrochemical cell based on the sensitization to light of photoactive molecules, and also to a photoelectrochemical cell based on the sensitization to light of photoactive molecules comprising an electrolyte composition comprising at least one halogenated histidine derivative as electrolyte salt.

17 Claims, 5 Drawing Sheets

(52) U.S. Cl.
CPC ......... *H01G 9/2027* (2013.01); *H01G 9/2059* (2013.01); *H01G 9/2031* (2013.01); *Y02E 10/542* (2013.01)

(56) References Cited

OTHER PUBLICATIONS

Dubey et al., "Facile Syntheses of Histamine- and Imidazole-4-propionic Acid-Derived Room-Temperature Ionic Liquids," Synthetic Comm., vol. 42, pp. 2207-2216 (2011) (Year: 2011).*

International Search Report dated Feb. 11, 2015.

Ravi Kant Dubey et al. "Facile Syntheses of Histamine and Imidazole-4-propionic Acid-Derived Room-Temperature Ionic Liquids," Synthetic Communications, Aug. 1, 2012.

Xiu Xu et al. "Performance Enhancement of Dye-sensitized Solar cells using an Ester-Functionalized Imidazolium Iodine as the Solid State Electrolyte" ACS Applied Materials & Interfaces, Apr. 24, 2013.

* cited by examiner

USE OF HALOGEN DERIVATIVES OF HISTIDINE AS ELECTROLYTIC SALT IN A PHOTOVOLTAIC DYE CELL

RELATED APPLICATION

This application is a National Phase of PCT/FR2015/052984, filed on Nov. 4, 2015 which in turn claims the benefit of priority from French Patent Application No. 14 60661, filed on Nov. 5, 2016, the entirety of which are incorporated by reference.

BACKGROUND

Field of the Invention

The present invention relates to the use of halogenated histidine derivatives as electrolyte salts in the preparation of an electrolyte composition in a photoelectrochemical cell based on the sensitization to light of photoactive molecules, and also to a photoelectrochemical cell based on the sensitization to light of photoactive molecules comprising an electrolyte composition comprising at least one halogenated histidine derivative as electrolyte salt.

The field of the invention may be defined as that of photoelectrochemical cells based on the sensitization to light of photoactive molecules, and more particularly dye-sensitized photovoltaic conversion cells (or dye-sensitized solar cells).

Description of Related Art

The most widespread photovoltaic cells ("first-generation solar cells") consist of bulk semiconductors, mainly based on amorphous or monocrystalline silicon (Si). They are generally provided in the form of thin sheets having a side length of approximately ten centimeters with p-doped zones and n-doped zones, in order to create a p-n junction. The semiconductor constitutes the "photoactive" medium inside which light is absorbed, thus creating electron-hole pairs. These sheets are sandwiched between two metal contacts, for a thickness of the order of a millimeter. The most effective silicon-based cells comprise an active layer of monocrystalline silicon, the conversion efficiency of which can reach 40% in the laboratory.

However, although very effective, photovoltaic cells based on silicon and in particular on monocrystalline silicon exhibit the major advantage of being expensive due to the high cost related to this starting material and its transformation. This is why a portion of research has been directed toward cells based on thin film semiconductors.

This is because thin film technology makes it possible to reduce the amount of semiconductors used and in addition makes possible the use of inexpensive substrates which may be flexible and have a high surface area. In thin film photovoltaic cells ("second-generation solar cells"), using, as semicrystalline material, silicon (amorphous silicon or crystalline silicon, in general polycrystalline silicon), copper indium diselenide (CIS) or cadmium telluride (CdTe), the thin films of material (of the order of a micron) are deposited on a substrate, for example made of glass. However, although having a lower cost price than first-generation solar cells, photovoltaic conversion cells based on thin films made of amorphous silicon are subject to problems of stability when they are exposed to the sun. Furthermore, as a result of its disorderly structure, the charge transportation properties of amorphous silicon are mediocre, resulting in a mediocre efficiency. Thus, a fall in efficiency of these cells of 10 to 50% takes place during the first approximately one hundred hours of exposure to light of the cells based on amorphous silicon.

Cells based on organic semiconductors and in particular on organometallic compounds, the cost price of which is lower than that of silicon, have also been proposed (third-generation solar cells). Their use in the photovoltaic field is based on the ability of some π-conjugated polymers and oligomers, or else of some π-conjugated small molecules, to convert light energy into electrical energy. When a p-n junction composed of two semiconductors having different natures, among which at least one is an organic compound, is formed, a heterojunction is thus defined.

Another type of solar cell consists of photovoltaic cells based on the sensitization to light of photoactive molecules (or dye-sensitized solar cells, known as "Graetzel cells"). These cells differentiate the functions of absorption of the light and of separation of the electric charges and are inspired by photosynthesis. Dye-sensitized solar cells consist of a photoanode comprising a layer of nanoparticles of a semiconducting oxide, such as, for example, titanium dioxide, on which a dye (or "sensitizer") is adsorbed, a counterelectrode comprising a platinum catalyst and an electrolyte which separates the photoanode from the counterelectrode, said electrolyte including a red/ox ion pair. Under the effect of solar radiation, the dye is excited by the incident photons absorbed and gains sufficient energy to be able to inject an electron into the conduction band of the semiconducting oxide. These cells exhibit the advantage that the materials which they use are relatively inexpensive.

Among the constituents of dye-sensitized solar cells, the electrolyte is the constituent which determines the lifetime of the cell, and also its performance, in particular the fill factor (FF) and the efficiency of the light conversion (Eff). The electrolytes of current dye-sensitized solar cells are liquids, in particular halogenated ionic liquids ($I^-$, $Br^-$), or gels based on the $I_3^-/I^-$ redox pair.

Provision has in particular already been made, especially in the international application WO 2010/117871, to use halides formed of a cation comprising one or more groups containing at least one quaternary nitrogen atom, one tertiary sulfur atom or one quaternary phosphorous atom and of an anion comprising a halide ion ($Br^-$ or $I^-$). According to this international application, the cation containing at least one quaternary nitrogen atom can in particular be a group of imidazolium or triazolium type and especially a 1,3-dialkylimidazolium group.

However, the use of these ionic liquids is not entirely satisfactory insofar as dialkylimidazolium halides in particular are highly hygroscopic compounds (approximately 30% loss in weight perceptible due to the presence of water) and their use in the electrolytes of solar cells presents a number of disadvantages. This is because, insofar as the presence of water is harmful for stability of solar cells, dialkylimidazolium halides and very particularly dialkylimidazolium iodides have to be stored under anhydrous conditions and absolutely have to be dried before being used in the manufacture of solar cells, if the stability of the latter is not to be seen to be detrimentally affected on a major scale. Compounds derived from imidazole are furthermore generally synthesized from oil-bearing resources, which is not satisfactory from the viewpoint of the protection of the environment and renewable energy.

Objects and Summary

There thus exists a need for compounds which can be used as electrolyte salts in an electrolyte composition of a photoelectrochemical cell based on the sensitization to light of photoactive molecules and in particular in a dye-sensitized photovoltaic cell, said compounds not exhibiting the disadvantages of the compounds used in the prior art, in particular for non-hygroscopic compounds, and which can be synthesized in a simple and relatively inexpensive way from starting materials not originating from oil-bearing resources.

The inventors have now discovered that some halides derived from L-histidine, the formula of which will be defined below, exhibit excellent electrolytic properties, which allows them to be advantageously used for as electrolyte salt of an electrolyte composition in a photoelectrochemical cell based on the sensitization to light of photoactive molecules and in particular in a dye-sensitized photovoltaic cell.

A first subject matter of the present invention is thus the use of at least one halide of following formula (I):

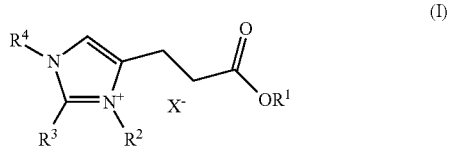

in which:
$R^1$ represents a hydrogen atom or a linear alkyl radical having from 1 to 10 carbon atoms;
$R^2$ and $R^4$, which are identical or different, each represent a linear or branched alkyl radical having from 1 to 15 carbon atoms, preferably from 1 to 6 carbon atoms, said alkyl radical optionally being substituted by one or more $C_6$-$C_{20}$ aryl groups which can optionally comprise one or more heteroatoms chosen from oxygen, sulfur and nitrogen atoms;
$R^3$ represents a hydrogen atom or a linear or branched alkyl radical having from 1 to 15 carbon atoms, preferably from 1 to 6 carbon atoms,
$X^-$ represents an iodide or bromide anion,
as electrolyte salt in an electrolyte composition of a photoelectrochemical cell based on the sensitization to light of photoactive molecules and in particular in a dye-sensitized photovoltaic cell.

The compounds of formula (I) defined above can be easily obtained from L-histidine under mild conditions, L-histidine being an amino acid not dependent on oil-bearing resources. Furthermore, these compounds are not hygroscopic and do not require any specific precautions for storage or use in the manufacture of photoelectrochemical cells based on the sensitization to light of photoactive molecules and in particular of dye-sensitized photovoltaic cells. Furthermore, the dye-sensitized photovoltaic cells incorporating such compounds as electrolyte exhibit improved performances with respect to equivalent dye-sensitized photovoltaic cells employing an imidazolium halide as electrolyte, in particular in terms of thermal stability, from the viewpoint of the standard protocol for aging defined by the standard IEC 61646 (for "International Electrotechnical Commission", which is an international organization for standardization in charge of the fields of electricity, electronics and related technologies). The standard IEC 61646 is concerned with photovoltaic cells of thin film type (for terrestrial application) and certifies a guarantee of quality as regards mechanical stability and in respect of the electrical parameters of the cell, the aim being to show that the cell is capable of withstanding prolonged exposure to the climates defined in the field of application. Finally, the dye-sensitized photovoltaic cells incorporating such compounds of formula (I) as electrolyte generate more photocurrent (approximately +2 mA/cm²) than an equivalent cell employing an imidazolium halide as electrolyte.

Mention may more particularly be made, among the $C_1$-$C_6$ alkyl radicals mentioned for the $R^1$ to $R^4$ radicals, of the methyl, ethyl, n-propyl or n-butyl radicals. Preference is given, among these radicals, to the methyl, ethyl and n-propyl radicals.

Iodides are preferred among the halides of formula (I) above.

Mention may in particular be made, among the compounds of formula (I) above, of:
4-(3-methoxy-3-oxopropyl)-1,3-dimethyl-1H-imidazol-3-ium iodide,
4-(3-ethoxy-3-oxopropyl)-1,3-dimethyl-1H-imidazol-3-ium iodide,
4-(3-methoxy-3-oxopropyl)-1,3-diethyl-1H-imidazol-3-ium iodide,
4-(3-methoxy-3-oxopropyl)-1,3-dipropyl-1H-imidazol-3-ium iodide,
4-(3-methoxy-3-oxopropyl)-1,3-dibutyl-1H-imidazol-3-ium iodide,
4-(3-methoxy-3-oxopropyl)-1,3-dipentyl-1H-imidazol-3-ium iodide,
4-(3-methoxy-3-oxopropyl)-1,3-dihexyl-1H-imidazol-3-ium iodide,
4-(3-methoxy-3-oxopropyl)-1-methyl-3-propyl-1H-imidazol-3-ium iodide,
3-ethyl-4-(3-methoxy-3-oxopropyl)-1-methyl-1H-imidazol-3-ium iodide,
4-(3-methoxy-3-oxopropyl)-1-methyl-3-propyl-1H-imidazol-3-ium iodide,
3-butyl-4-(3-methoxy-3-oxopropyl)-1-methyl-1H-imidazol-3-ium iodide,
4-(3-methoxy-3-oxopropyl)-1-methyl-3-pentyl-1H-imidazol-3-ium iodide,
3-hexyl-4-(3-methoxy-3-oxopropyl)-1-methyl-1H-imidazol-3-ium iodide,
1-ethyl-4-(3-methoxy-3-oxopropyl)-3-methyl-1H-imidazol-3-ium iodide,
1,3-diethyl-4-(3-methoxy-3-oxopropyl)-1H-imidazol-3-ium iodide,
1-ethyl-4-(3-methoxy-3-oxopropyl)-3-propyl-1H-imidazol-3-ium iodide,
3-butyl-1-ethyl-4-(3-methoxy-3-oxopropyl)-1H-imidazol-3-ium iodide,
1-ethyl-4-(3-methoxy-3-oxopropyl)-3-pentyl-1H-imidazol-3-ium iodide,
1-ethyl-3-hexyl-4-(3-methoxy-3-oxopropyl)-1H-imidazol-3-ium iodide,
4-(3-methoxy-3-oxopropyl)-3-methyl-1-propyl-1H-imidazol-3-ium iodide,
3-ethyl-4-(3-methoxy-3-oxopropyl)-1-propyl-1H-imidazol-3-ium iodide,
4-(3-methoxy-3-oxopropyl)-1,3-dipropyl-1H-imidazol-3-ium iodide,
3-butyl-4-(3-methoxy-3-oxopropyl)-1-propyl-1H-imidazol-3-ium iodide,
4-(3-methoxy-3-oxopropyl)-3-pentyl-1-propyl-1H-imidazol-3-ium iodide,
3-hexyl-4-(3-methoxy-3-oxopropyl)-1-propyl-1H-imidazol-3-ium iodide,
1-butyl-4-(3-methoxy-3-oxopropyl)-3-methyl-1H-imidazol-3-ium iodide, 1-butyl-3-ethyl-4-(3-methoxy-3-oxopropyl)-1H-imidazol-3-ium iodide,
1-butyl-4-(3-methoxy-3-oxopropyl)-3-propyl-1H-imidazol-3-ium iodide,
1,3-dibutyl-4-(3-methoxy-3-oxopropyl)-1H-imidazol-3-ium iodide,
1-butyl-4-(3-methoxy-3-oxopropyl)-3-pentyl-1H-imidazol-3-ium iodide,
1-butyl-3-hexyl-4-(3-methoxy-3-oxopropyl)-1H-imidazol-3-ium iodide,
4-(3-methoxy-3-oxopropyl)-3-methyl-1-pentyl-1H-imidazol-3-ium iodide,
3-ethyl-4-(3-methoxy-3-oxopropyl)-1-pentyl-1H-imidazol-3-ium iodide,
4-(3-methoxy-3-oxopropyl)-1-pentyl-3-propyl-1H-imidazol-3-ium iodide,
3-butyl-4-(3-methoxy-3-oxopropyl)-1-pentyl-1H-imidazol-3-ium iodide,
4-(3-methoxy-3-oxopropyl)-1,3-dipentyl-1H-imidazol-3-ium iodide,
3-hexyl-4-(3-methoxy-3-oxopropyl)-1-pentyl-1H-imidazol-3-ium iodide,
1-hexyl-4-(3-methoxy-3-oxopropyl)-3-methyl-1H-imidazol-3-ium iodide,
3-ethyl-1-hexyl-4-(3-methoxy-3-oxopropyl)-1H-imidazol-3-ium iodide,
1-hexyl-4-(3-methoxy-3-oxopropyl)-3-propyl-1H-imidazol-3-ium iodide,
3-butyl-1-hexyl-4-(3-methoxy-3-oxopropyl)-1H-imidazol-3-ium iodide,
1-hexyl-4-(3-methoxy-3-oxopropyl)-3-pentyl-1H-imidazol-3-ium iodide,
1,3-dihexyl-4-(3-methoxy-3-oxopropyl)-1H-imidazol-3-ium iodide,
3-ethyl-4-(3-methoxy-3-oxopropyl)-1-methyl-1H-imidazol-3-ium bromide,
4-(3-methoxy-3-oxopropyl)-1-methyl-3-propyl-1H-imidazol-3-ium bromide,
3-butyl-4-(3-methoxy-3-oxopropyl)-1-methyl-1H-imidazol-3-ium bromide,
4-(3-methoxy-3-oxopropyl)-1-methyl-3-pentyl-1H-imidazol-3-ium bromide,
3-hexyl-4-(3-methoxy-3-oxopropyl)-1-methyl-1H-imidazol-3-ium bromide,
1-ethyl-4-(3-methoxy-3-oxopropyl)-3-methyl-1H-imidazol-3-ium bromide,
1,3-diethyl-4-(3-methoxy-3-oxopropyl)-1H-imidazol-3-ium bromide,
1-ethyl-4-(3-methoxy-3-oxopropyl)-3-propyl-1H-imidazol-3-ium bromide,
3-butyl-1-ethyl-4-(3-methoxy-3-oxopropyl)-1H-imidazol-3-ium bromide,
1-ethyl-4-(3-methoxy-3-oxopropyl)-3-pentyl-1H-imidazol-3-ium bromide,
1-ethyl-3-hexyl-4-(3-methoxy-3-oxopropyl)-1H-imidazol-3-ium bromide,
4-(3-methoxy-3-oxopropyl)-3-methyl-1-propyl-1H-imidazol-3-ium bromide,
3-ethyl-4-(3-methoxy-3-oxopropyl)-1-propyl-1H-imidazol-3-ium bromide,
4-(3-methoxy-3-oxopropyl)-1,3-dipropyl-1H-imidazol-3-ium bromide,
3-butyl-4-(3-methoxy-3-oxopropyl)-1-propyl-1H-imidazol-3-ium bromide,
4-(3-methoxy-3-oxopropyl)-3-pentyl-1-propyl-1H-imidazol-3-ium bromide,
3-hexyl-4-(3-methoxy-3-oxopropyl)-1-propyl-1H-imidazol-3-ium bromide,
1-butyl-4-(3-methoxy-3-oxopropyl)-3-methyl-1H-imidazol-3-ium bromide,
1-butyl-3-ethyl-4-(3-methoxy-3-oxopropyl)-1H-imidazol-3-ium bromide,
1-butyl-4-(3-methoxy-3-oxopropyl)-3-propyl-1H-imidazol-3-ium bromide,
1,3-dibutyl-4-(3-methoxy-3-oxopropyl)-1H-imidazol-3-ium bromide,
1-butyl-4-(3-methoxy-3-oxopropyl)-3-pentyl-1H-imidazol-3-ium bromide,
1-butyl-3-hexyl-4-(3-methoxy-3-oxopropyl)-1H-imidazol-3-ium bromide,
4-(3-methoxy-3-oxopropyl)-3-methyl-1-pentyl-1H-imidazol-3-ium bromide,
3-ethyl-4-(3-methoxy-3-oxopropyl)-1-pentyl-1H-imidazol-3-ium bromide,
4-(3-methoxy-3-oxopropyl)-1-pentyl-3-propyl-1H-imidazol-3-ium bromide,
3-butyl-4-(3-methoxy-3-oxopropyl)-1-pentyl-1H-imidazol-3-ium bromide,
4-(3-methoxy-3-oxopropyl)-1,3-dipentyl-1H-imidazol-3-ium bromide,
3-hexyl-4-(3-methoxy-3-oxopropyl)-1-pentyl-1H-imidazol-3-ium bromide,
1-hexyl-4-(3-methoxy-3-oxopropyl)-3-methyl-1H-imidazol-3-ium bromide,
3-ethyl-1-hexyl-4-(3-methoxy-3-oxopropyl)-1H-imidazol-3-ium bromide,
1-hexyl-4-(3-methoxy-3-oxopropyl)-3-propyl-1H-imidazol-3-ium bromide,
3-butyl-1-hexyl-4-(3-methoxy-3-oxopropyl)-1H-imidazol-3-ium bromide,
1-hexyl-4-(3-methoxy-3-oxopropyl)-3-pentyl-1H-imidazol-3-ium bromide,
1,3-dihexyl-4-(3-methoxy-3-oxopropyl)-1H-imidazol-3-ium bromide,
4-(3-methoxy-3-oxopropyl)-1,2,3-trimethyl-1H-imidazol-3-ium iodide,
3-ethyl-4-(3-methoxy-3-oxopropyl)-1,2-dimethyl-1H-imidazol-3-ium iodide,
4-(3-methoxy-3-oxopropyl)-1,2-dimethyl-3-propyl-1H-imidazol-3-ium iodide,
3-butyl-4-(3-methoxy-3-oxopropyl)-1,2-dimethyl-1H-imidazol-3-ium iodide,
4-(3-methoxy-3-oxopropyl)-1,2-dimethyl-3-pentyl-1H-imidazol-3-ium iodide,
3-hexyl-4-(3-methoxy-3-oxopropyl)-1,2-dimethyl-1H-imidazol-3-ium iodide,
1,3-diethyl-4-(3-methoxy-3-oxopropyl)-2-methyl-1H-imidazol-3-ium iodide,
4-(3-methoxy-3-oxopropyl)-2-methyl-1,3-dipropyl-1H-imidazol-3-ium iodide,
1,3-dibutyl-4-(3-methoxy-3-oxopropyl)-2-methyl-1H-imidazol-3-ium iodide,
4-(3-methoxy-3-oxopropyl)-2-methyl-1,3-dipentyl-1H-imidazol-3-ium iodide,
1,3-dihexyl-4-(3-methoxy-3-oxopropyl)-2-methyl-1H-imidazol-3-ium iodide,
1-ethyl-3-hexyl-4-(3-methoxy-3-oxopropyl)-2-methyl-1H-imidazol-3-ium iodide,
4-(3-methoxy-3-oxopropyl)-1-methyl-3-propyl-1H-imidazol-3-ium bromide,
4-(3-methoxy-3-oxopropyl)-1,2,3-trimethyl-1H-imidazol-3-ium bromide, 3-ethyl-4-(3-methoxy-3-oxopropyl)-1,2-dimethyl-1H-imidazol-3-ium bromide,
4-(3-methoxy-3-oxopropyl)-1,2-dimethyl-3-propyl-1H-imidazol-3-ium bromide,
3-butyl-4-(3-methoxy-3-oxopropyl)-1,2-dimethyl-1H-imidazol-3-ium bromide,
4-(3-methoxy-3-oxopropyl)-1,2-dimethyl-3-pentyl-1H-imidazol-3-ium bromide,
3-hexyl-4-(3-methoxy-3-oxopropyl)-1,2-dimethyl-1H-imidazol-3-ium bromide,
1,3-diethyl-4-(3-methoxy-3-oxopropyl)-2-methyl-1H-imidazol-3-ium bromide,
4-(3-methoxy-3-oxopropyl)-2-methyl-1,3-dipropyl-1H-imidazol-3-ium bromide,
1,3-dibutyl-4-(3-methoxy-3-oxopropyl)-2-methyl-1H-imidazol-3-ium bromide,
4-(3-methoxy-3-oxopropyl)-2-methyl-1,3-dipentyl-1H-imidazol-3-ium bromide,
and
1-ethyl-3-hexyl-4-(3-methoxy-3-oxopropyl)-2-methyl-1H-imidazol-3-ium iodide.

4-(3-Methoxy-3-oxopropyl)-1,3-dimethyl-1H-imidazol-3-ium iodide is a solid salt, the melting point of which is approximately 134.7° C. just like 4-(3-methoxy-3-oxopropyl)-1,3-dimethyl-1H-imidazol-3-ium iodide (melting point of approximately 111° C.) and 4-(3-ethoxy-3-oxopropyl)-1,3-dimethyl-1H-imidazol-3-ium iodide. The other compounds of formula (I) and in particular 4-(3-methoxy-3-oxopropyl)-1-methyl-3-propyl-1H-imidazol-3-ium iodide are viscous ionic liquids at ambient temperature.

Thermogravimetric analyses under air carried out by the inventors have shown that the compounds of formula (I) are stable up to a temperature of approximately 300° C., which represents a markedly greater stability to the conditions of accelerated aging of a solar cell according to the standard IEC 61646 (1000 hours at 60° C./100 mW·cm$^{-2}$ of illumination and 1000 hours at 85° C. in the dark).

The compounds of formula (I) as defined above can be prepared according to a simple and relatively inexpensive process starting from urocanic acid. If desired, the urocanic acid can be obtained by deamination of L-histidine of following formula:

L-Histidine by the enzymatic route in the presence of a histidinase to result in urocanic acid of following formula:

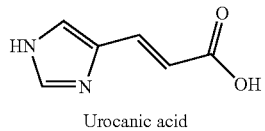

Urocanic acid

It is also possible to obtain urocanic acid directly insofar as it is a commercial product (CAS No. 104-98-3).

The process for the synthesis of the compounds of formula (I) subsequently varies as a function of the nature of the radicals defined for $R^1$ to $R^4$.

When $R^1$ is other than a hydrogen atom, that is to say when $R^1$ represents a linear alkyl radical having from 1 to 10 carbon atoms, the first stage of the process consists in carrying out the esterification of the carboxylic acid functional group of the urocanic acid in the presence of an alcohol $R'^1OH$ in order to obtain a compound (1), according to the following reaction (i):

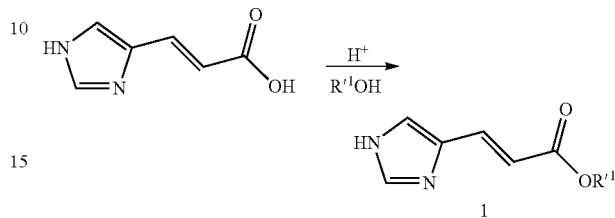

$R'^1$ being a linear alkyl radical having from 1 to 10 carbon atoms.

The reaction (i) is preferably carried out in an organic solvent which can, for example, be chosen from lower alcohols, such as ethanol, dimethylformamide (DMF), dimethyl sulfoxide (DMSO), toluene, tetrahydrofuran (THF), dichloromethane and dioxane, at a temperature varying from ambient temperature to the reflux temperature of the solvent used and at an acidic pH (of between 2 and 5 approximately).

The compound (1) is then hydrogenated in the presence of a catalyst, such as palladium-on-charcoal, to result in a compound (2) in which $R'^1$ represents a linear alkyl radical having from 1 to 10 carbon atoms, according to the following reaction (ii):

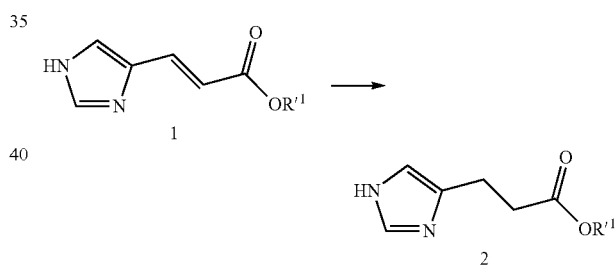

The reaction (ii) is preferably carried out in an organic solvent, such as methanol.

When it is desired to obtain a compound of formula (I) in which $R^3$ is a hydrogen atom and $R^4$ is an alkyl radical identical to the alkyl radical chosen for $R^2$ (compound (I-1)), the compound (2) is subsequently introduced into the following reaction (iii-a):

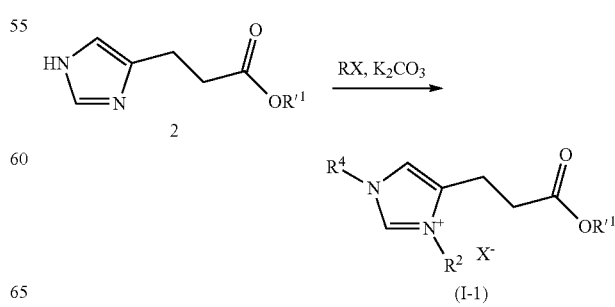

said reaction (iii-a) consisting in reacting said compound (2) with an alkyl or aryl halide RX in which X represents iodide or bromine and R is a linear or branched alkyl radical having from 1 to 15 carbon atoms, preferably from 1 to 6 carbon atoms, said alkyl radical optionally being substituted by one or more $C_6$-$C_{20}$ aryl groups which can optionally comprise one or more heteroatoms chosen from oxygen, sulfur and nitrogen atoms, said radical R being identical to the radicals $R^2$ and $R^4$ which it is desired to have on the compound (I-1), in an organic solvent, such as acetone, in the presence of potassium carbonate and at a temperature varying from ambient temperature to approximately 56° C.

The compounds of formula (I) in which $R^3$ is a hydrogen atom and $R^2$ is an alkyl or aryl radical different from the alkyl or aryl radical chosen for $R^4$ (compounds (I-2)) can be obtained from a compound (2) according to the following reaction (iii-b):

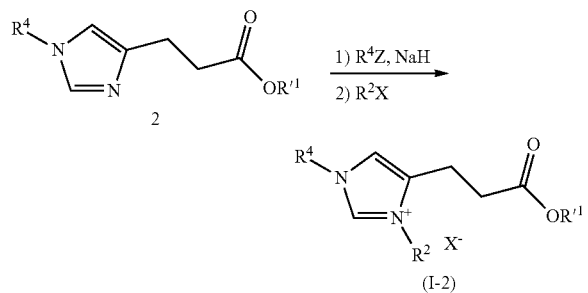

(I-2)

according to which, in a sub-stage 1), the alkylation of the nitrogen atom in the 1 position of the imidazole ring by an alkyl or aryl halide of formula $R^4Z$ in which $R^4$ is a linear or branched alkyl radical having from 1 to 15 carbon atoms, preferably from 1 to 6 carbon atoms, said alkyl radical optionally being substituted by one or more $C_6$-$C_{20}$ aryl groups which optionally comprise one or more heteroatoms chosen from oxygen, sulfur and nitrogen atoms, and Z represents a halogen atom (Cl, Br, I) is carried out and then, in a sub-stage 2), the intermediate compound thus obtained is reacted with an alkyl or aryl halide RX in which X is iodine or bromine and R is a linear or branched alkyl radical having from 1 to 15 carbon atoms, preferably from 1 to 6 carbon atoms, said alkyl radical optionally being substituted by one or more $C_6$-$C_{20}$ aryl groups which can optionally comprise one or more heteroatoms chosen from oxygen, sulfur and nitrogen atoms, R furthermore being identical to or different from $R^4$.

Sub-stage 1) of the reaction (iii-a) can be carried out in an organic solvent, such as, for example, dimethylformamide, in the presence of a strong base, such as, for example, sodium hydride. Sub-stage 2) of the reaction (iii-b) can be carried out under the same conditions as stage (iii-a) above.

The compounds of formula (I) in which $R^2$ and $R^4$, which are identical or different, represent a linear or branched alkyl radical having from 1 to 15 carbon atoms, preferably from 1 to 6 carbon atoms, said alkyl radical optionally being substituted by one or more $C_6$-$C_{20}$ aryl groups which can optionally comprise one or more heteroatoms chosen from oxygen, sulfur and nitrogen atoms, and $R^3$ represents a linear alkyl radical having from 1 to 15 carbon atoms, preferably from 1 to 6 carbon atoms, (compound (I-3)) can be obtained from a compound (2) according to the following reaction (iii-c):

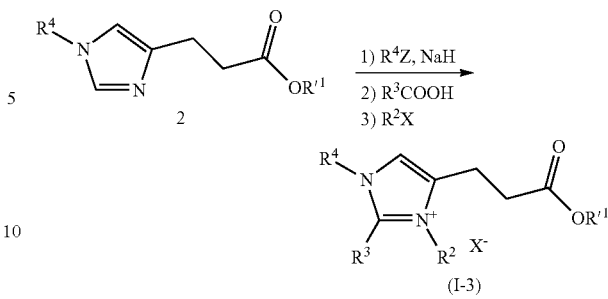

(I-3)

Sub-stage 1) can be carried out under the same conditions as sub-stage 1) of the reaction (iii-b). Sub-stage 2) is carried out in the presence of a carboxylic acid of the formula $R^3COOH$ in which $R^3$ represents a hydrogen atom or a linear alkyl radical having from 1 to 15 carbon atoms, preferably from 1 to 6 carbon atoms. Sub-stage 2) is preferably carried out at acidic pH in an organic solvent, such as, for example, methanol, water, toluene or dioxane, in the presence of silver nitrate and of an oxidizing agent, such as ammonium persulfurte, at a temperature of between ambient temperature and the reflux temperature of the solvent used. Sub-stage 3) can be carried out in an organic solvent, such as, for example, acetone, or without solvent at a temperature of between ambient temperature and the reflux temperature of the solvent used, if appropriate, using a compound of formula $R^2X$ in which $R^2$ is a linear or branched alkyl radical having from 1 to 15 carbon atoms, preferably from 1 to 6 carbon atoms, said alkyl radical optionally being substituted by one or more $C_6$-$C_{20}$ aryl groups which can optionally comprise one or more heteroatoms chosen from oxygen, sulfur and nitrogen atoms and X represents the iodine atom.

The compounds of formula (I) in which $R^1$ is a hydrogen atom can be obtained by deprotection of the carboxylic acid functional group of a compound of formula (I-1), (I-2) or (I-3) as described above, following the compound of formula (I) which it is desired to obtain. The stage of deprotection of the carboxylic acid functional group is preferably carried out at basic pH in water at a temperature of between ambient temperature and the reflux temperature of the water.

This process is simple and relatively inexpensive to carry out and it makes possible access to the compounds of formula (I) with a very good yield.

As has been seen above, the compounds of formula (I) are nonhygroscopic compounds which can thus be advantageously used as electrolyte salt of a reversible redox pair in an electrolyte composition of a photoelectrochemical cell based on sensitization to light of photoactive molecules and in particular of a dye-sensitized photovoltaic cell.

Another subject matter of the invention is thus a photoelectrochemical cell based on the sensitization to light of photoactive molecules comprising:
   an assembly forming a photoelectrode comprising:
      i) a transparent substrate coated with a layer of a transparent and conducting electrode material,
      ii) a photoactive layer formed on said electrode material, said photoactive layer comprising a transparent carrier material and at least one photoactive molecule;
   an assembly forming a counterelectrode; and
   an electrolyte composition interposed between said photoactive layer and said counterelectrode, said cell being characterized in that said electrolyte composition comprises, in an electrolyte solvent, a reversible redox pair ($I_3^-/I^-$) based on molecular iodine and on at least one compound of formula (I) as defined above.

According to a preferred embodiment of the invention, the photoelectrochemical cell based on the sensitization to light of photoactive molecules is a dye-sensitized photovoltaic cell. Also preferably, the photoelectrode is a photoanode.

The compound of formula (I) is preferably chosen from 4-(3-methoxy-3-oxopropyl)-1,3-dimethyl-1H-imidazol-3-ium iodide, 4-(3-methoxy-3-oxopropyl)-1-methyl-3-propyl-1H-imidazol-3-ium iodide, 4-(3-methoxy-3-oxopropyl)-1,3-dimethyl-1H-imidazol-3-ium bromide and 4-(3-methoxy-3-oxopropyl)-1-methyl-3-propyl-1H-imidazol-3-ium bromide, 4-(3-ethoxy-3-oxopropyl)-1,3-dimethyl-1H-imidazol-3-ium iodide, 4-(3-methoxy-3-oxopropyl)-1,3-diethyl-1H-imidazol-3-ium iodide, 4-(3-methoxy-3-oxopropyl)-1,3-dipropyl-1H-imidazol-3-ium iodide, 4-(3-methoxy-3-oxopropyl)-1,3-dibutyl-1H-imidazol-3-ium iodide, 4-(3-methoxy-3-oxopropyl)-1,3-dipentyl-1H-imidazol-3-ium iodide, and 4-(3-methoxy-3-oxopropyl)-1,3-dihexyl-1H-imidazol-3-ium iodide.

Preference is very particularly given, among these compounds of formula (I), to 4-(3-methoxy-3-oxopropyl)-1,3-dimethyl-1H-imidazol-3-ium iodide, 4-(3-methoxy-3-oxopropyl)-1-methyl-3-propyl-1H-imidazol-3-ium iodide, 4-(3-methoxy-3-oxopropyl)-1,3-dimethyl-1H-imidazol-3-ium bromide and 4-(3-methoxy-3-oxopropyl)-1-methyl-3-propyl-1H-imidazol-3-ium bromide.

According to a preferred embodiment of the invention, the concentration of the compound or compounds of formula (I) within the electrolyte composition varies from 0.1 to 5 mol/l approximately and more preferably still from 0.5 to 1.5 mol/l approximately.

The concentration of molecular iodine within the electrolyte composition preferably varies from 0.001 to 0.5 mol/l approximately and more preferably still from 0.01 to 0.2 mol/l approximately.

The electrolyte solvent or solvents can be chosen from nitriles, such as, for example, acetonitrile, propionitrile, methoxypropionitrile, methoxyacetonitrile, glutaronitrile, succinonitrile, 3-hydroxypropionitrile, benzonitrile, phenylacetonitrile, butyronitrile or valeronitrile; sulfolane; dimethyl sulfoxide; dioxane; tetrahydrofuran; nitromethane; amides, such as, for example, N,N-dimethylformamide or N,N-dimethylacetamide; N-methyl-2-pyrrolidinone; carbonates, such as, for example, propylene carbonate, ethylene carbonate, dimethylene carbonate or butylene carbonate; ethylene glycols, such as, for example, tetraglyme; alcohols, such as, for example, ethanol, methanol, ethoxyethanol, methoxyethanol, propanol, butanol or hexanol; ketones, such as, for example, cyclopentanone or benzylacetone; lactones, such as gamma-butyrolactone or acetylbutyrolactone; anhydrides, such as, for example, acetic anhydride; ethers, such as, for example, 2-methoxyethyl ether; water; phthalates; adipates; citrates; sebacates; maleates; benzoates and succinates.

The solvent or solvents of the electrolyte can also be chosen from ionic liquids. Ionic liquids are salts comprising the combination of an anion and of a cation in stoichiometric proportions providing the salt with electrical neutrality. The most widely used cations have a structure of the ammonium, imidazolium, pyridinium, pyrrolidinium, phosphonium, thiazolium, quinolinium or tetraminium type. The anions are preferably chosen from halides other than iodine (F, Cl, Br); tetrafluoroborate ($BF_4$), hexafluorophosphate (PF6), sulfurte ($SO_4$) and hydrogen sulfurte ($HSO_4$) anions; carboxylate anions, for example formate (HCOO), acetate ($CH_3COO$), trifluoroacetate ($CF_3COO$) and propanoate ($CH_3$—$CH_2$—COO); sulfonylimide anions, for example bis((trifluoromethylsulfonylimide (($CF_3$—$SO_2$)$_2$N) and bis(methylsulfonyl)imide (($CH_3$—$SO_2$)$_2$N) anions; the dicyanamide ($N(CN)_2$) anion; sulfonate anions, such as, for example, methylsulfonate ($CH_3SO_3$), trifluoromethylsulfonate ($CF_3SO_3$), benzenesulfonate ($C_6H_5$—$SO_3$), p-toluenesulfonate ($CH_3$—$C_6H_4$—$SO_3$) and perfluorobutylsulfonate ($C_4F_9SO_3$); sulfinate anions, such as, for example, trifluoromethanesulfinate ($CF_3SO_2$) and perfluorobutylsulfinate ($C_4F_9SO_2$); phosphate anions, such as, for example, dimethyl phosphate (($CH_3O)_2PO_2$), diethyl phosphate (($C_2H_5O)_2PO_2$), dihydrogenphosphate ($H_2PO_4$), hydrogenphosphate ($HPO_4$) and phosphate ($PO_4$); phosphonate anions, such as, for example, methylphosphonate ($CH_3PO_3H$) and ethylphosphonate ($C_2H_5PO_3H$); and other anions, such as, for example, hexafluoroarsenate ($AsF_6$), hexafluoroniobate ($NbF_6$) and hexafluoroantimonate ($SbF_6$).

When an ionic liquid is used as solvent of the electrolyte composition, the anion of said ionic liquid must specifically be different from the iodide anion so as not to interfere with the reversible redox pair ($I_3^-/I^-$) based on molecular iodine and on at least one compound of formula (I).

Mention may more particularly be made, among the abovementioned ionic liquids, of 1-ethyl-3-methylimidazolium bis(trifluoromethanesulfonyl)imide (EMI-TFSI), 1-butyl-3-methylimidazolium bis(trifluoromethanesulfonyl)imide (BMI-TFSI), 1-butyl-3-methylimidazolium hexafluorophosphate (BMI-PF$_6$), 1-butyl-1-methylpyrrolidinium bis(trifluoromethylsulfonyl)imide and their mixtures. Among these ionic liquids, BMI-TFSI is particularly preferred due to its wide electrochemical window.

The electrolyte composition can in addition include one or more additives intended to improve the performance of the photoelectrochemical cell. Such additives can in particular be chosen from benzimidazole derivatives, such as, for example, N-methylbenzimidazole and N-butylbenzimidazole; pyridine derivatives, such as, for example, tert-butylpyridine (TBP); triazole derivatives, such as, for example, N,N-dipropyl-4H-1,2,4-triazol-4-amine; pyrazole derivatives, such as, for example, 5-(tert-butyl)-1H-pyrazol-3-amine; imidazole derivatives, such as, for example, 1,2-dimethyl-1H-imidazole; ethylene carbonate; guanidine thiocyanate; chenodeoxycholic acid; magnesium iodide; and alkali metal salts of formula LiY or NaY in which Y can in particular be an $I^-$, $Br^-$, trifluorosulfonate, $ClO_4^-$, $NO_3^-$ or TFSI$^-$ anion.

The concentration of these additives within the electrolytic composition can then preferably vary from 0.01 to 1 mol/l approximately and more preferably still from 0.05 to 0.5 mol/l.

The electrolyte composition can also additionally include at least one gelling agent, so as to form a gel. The gelling agent can in particular be chosen from copolymers of ethylene, of vinyl acetate, of ethylene/vinyl acetate (EVA), polyurethanes (PU), polyvinyl butyral (PVB), polyimides (PI), polyamides (PA), polystyrene (PS), poly(vinylidene fluoride) (PVDF), polyether ketones (PEK), polyether ether ketones (PEEK), epichlorohydrin copolymers, polyolefins, poly(ethylene oxide) (PEO), polyacrylates, poly(methyl methacrylate) (PMMA), silicones or their derivatives or their monomers or else their prepolymers.

The concentration of these gelling agents within the electrolytic composition can then preferably vary from 0.01 to 1 mol/l approximately and more preferably still from 0.05 to 0.5 mol/l.

The transparent substrate of the photoelectrode is made of a material which can be flexible or rigid, for example glass or a sheet made of a plastic material, such as, for example, made of a material based on polyethylene terephthalate (PET), on polyethylene naphthalate (PEN), on polycarbonate (PC), on polyimide (PI) or on fluorinated substrates.

The electrode material of the photoelectrode is applied to the transparent substrate. It is generally provided in the form of a layer of a transparent conducting oxide (TCO), such as layers of tin oxide doped with fluorine ($SnO_2$:F or FTO), of indium tin oxide ($In_2O_3$:$SnO_2$ or ITO), of indium oxide doped with antimony ($In_2O_3$:Sb) and of zinc oxide doped with aluminum (ZnO:Al), with gallium (ZnO:Ga) or with indium (ZnO:In).

The transparent carrier material of the photoactive layer of the photoanode is preferably a mesoporous layer of a metal oxide, for example based on titanium oxide, on zinc oxide, on tin oxide, on niobium oxide, on tungsten oxide, on strontium oxide, on zirconium oxide or on one of their mixtures. According to a particularly preferred embodiment of the invention, the transparent carrier material of the photoactive layer of the photoanode is a nanoporous layer of titanium oxide or of a ternary oxide based on titanium, on tin or on zinc, such as, for example, $BaTiO_3$, $BaSnO_3$, $Li_4Ti_5O_{12}$ and $ZnSn_2O_4$.

The photoactive molecule of the photoactive layer can be chosen from all the dyes generally used in dye-sensitized photovoltaic cells and which are well known to a person skilled in the art. Mention may in particular be made of organic dyes of the series of the cyanines, merocyanines, oxonols, xanthenes, squaryliums, polymethines, coumarins, riboflavins and perylenes, dye complexes, such as ruthenium or osmium complexes, metal phthalocyanine derivatives, metal porphyrin derivatives or chlorophyll derivatives.

Mention may more particularly be made, among ruthenium complexes, of the ruthenium complexes containing pyridyl ligands, such as, for example the hydrophobic heteroleptic complex of formula RuLL'$(NCS)_2$ with L=2,2'-bipyridyl-4,4'-dicarboxylic acid and L'=4,4'-bis(5-(hexylthio)thiophen-2-yl)-2,2'-bipyridine.

The photoactive molecule is adsorbed on the carrier material, for example by immersion of the carrier material in a solution containing this photoactive molecule.

The counterelectrode preferably consists of a transparent counter substrate coated with a layer of a material forming the transparent counterelectrode, such as a layer of $SnO_2$:F or of doped ZnO, or with a stack of transparent conducting layers, such as, for example, a glass+TCO or metal assembly. The countersubstrate can be chosen from the same substrates as those mentioned above for the transparent substrate of the photoanode.

A layer of catalyst is furthermore formed on the material forming the counterelectrode, it being possible for the layer of catalyst, for example, to be a layer of platinum or of carbon or of inorganic chalcogenide.

The photovoltaic cell according to the invention can be prepared according to the techniques known to a person skilled in the art and such as, for example, by roll coating or roll-to-roll, flexography, screen printing, cathode sputtering, dip coating, spin coating, application with a doctor blade, and the like, or a mixture of these techniques. The assembled systems can be monolithic or laminated in an open or closed structure.

Finally, some of the compounds of formula (I) above are novel per se and constitute as such another subject-matter of the invention. These compounds correspond to the following formula (I'):

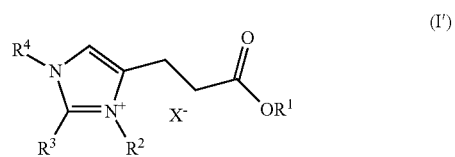

in which:
$R^1$ represents a hydrogen atom or a linear alkyl radical having from 1 to 10 carbon atoms,
$R^2$ and $R^4$, which are identical or different, each represent a linear or branched alkyl radical having from 1 to 15 carbon atoms, preferably from 1 to 6 carbon atoms, said alkyl radical optionally being substituted by one or more $C_6$-$C_{20}$ aryl groups which can optionally comprise one or more heteroatoms chosen from oxygen, sulfur and nitrogen atoms,
$R^3$ represents a hydrogen atom or a linear or branched alkyl radical having from 1 to 15 carbon atoms,
$X^-$ represents an iodide or bromide anion,
it being understood that:
when $X^-$ represents an iodide anion, when $R^1$ represents a methyl radical and when $R^3$ is a hydrogen atom, then the $R^2$ and $R^4$ radicals cannot simultaneously represent a methyl radical or an ethyl radical,
when $X^-$ represents a bromide anion, when $R^1$ represents a methyl radical and when $R^3$ is a hydrogen atom, then the $R^2$ and $R^4$ radicals cannot simultaneously represent a benzyl radical,
when $X^-$ represents a bromide anion, when $R^1$ represents a methyl radical, when $R^2$ is a butyl radical and when $R^3$ is a hydrogen atom, then the $R^4$ radical is other than a methyl, ethyl or benzyl radical,
when $X^-$ represents an iodide anion, when $R^1$ and $R^2$ represent a methyl radical and when $R^3$ is a hydrogen atom, then the $R^4$ radical is other than a trityl radical, and
when $X^-$ represents a bromide anion, when $R^1$ represents a methyl radical, when $R^2$ is a butyl radical and when $R^3$ is an isopropyl radical, then the $R^4$ radical is other than a methyl radical.

The compounds excluded from the above formula (I') are compounds which have already been described as ionic liquid in the paper by R. K. Dubey et al., Synthetic Communications, 2012, 42, 2207-2216, or in the international application WO 2010/052253, which describes in particular the use of 5-(2-methoxycarbonylethyl)-1-methyl-3-trityl-3H-imidazolium iodide as intermediate compound in the synthesis of oxoazetidine derivatives of use in human medicine or in cosmetics. Their use as electrolyte salt in an electrolyte composition of a photoelectrochemical cell has, however, never been described.

The compounds of formula (I') can be prepared according to the same process as that used to prepare the compounds of formula (I) described in detail above.

Mention may in particular be made, among the compounds of formula (I') above, of:
4-(3-ethoxy-3-oxopropyl)-1,3-dimethyl-1H-imidazol-3-ium iodide,
4-(3-methoxy-3-oxopropyl)-1,3-dipropyl-1H-imidazol-3-ium iodide,
4-(3-methoxy-3-oxopropyl)-1,3-dibutyl-1H-imidazol-3-ium iodide,
4-(3-methoxy-3-oxopropyl)-1,3-dipentyl-1H-imidazol-3-ium iodide, 4-(3-methoxy-3-oxopropyl)-1,3-dihexyl-1H-imidazol-3-ium iodide,
3-ethyl-4-(3-methoxy-3-oxopropyl)-1-methyl-1H-imidazol-3-ium iodide,
4-(3-methoxy-3-oxopropyl)-1-methyl-3-propyl-1H-imidazol-3-ium iodide,
3-butyl-4-(3-methoxy-3-oxopropyl)-1-methyl-1H-imidazol-3-ium iodide,
4-(3-methoxy-3-oxopropyl)-1-methyl-3-pentyl-1H-imidazol-3-ium iodide,
3-hexyl-4-(3-methoxy-3-oxopropyl)-1-methyl-1H-imidazol-3-ium iodide,
1-ethyl-4-(3-methoxy-3-oxopropyl)-3-methyl-1H-imidazol-3-ium iodide,
1-ethyl-4-(3-methoxy-3-oxopropyl)-3-propyl-1H-imidazol-3-ium iodide,
3-butyl-1-ethyl-4-(3-methoxy-3-oxopropyl)-1H-imidazol-3-ium iodide,
1-ethyl-4-(3-methoxy-3-oxopropyl)-3-pentyl-1H-imidazol-3-ium iodide,
1-ethyl-3-hexyl-4-(3-methoxy-3-oxopropyl)-1H-imidazol-3-ium iodide,
4-(3-methoxy-3-oxopropyl)-3-methyl-1-propyl-1H-imidazol-3-ium iodide,
3-ethyl-4-(3-methoxy-3-oxopropyl)-1-propyl-1H-imidazol-3-ium iodide,
4-(3-methoxy-3-oxopropyl)-1,3-dipropyl-1H-imidazol-3-ium iodide,
3-butyl-4-(3-methoxy-3-oxopropyl)-1-propyl-1H-imidazol-3-ium iodide,
4-(3-methoxy-3-oxopropyl)-3-pentyl-1-propyl-1H-imidazol-3-ium iodide,
3-hexyl-4-(3-methoxy-3-oxopropyl)-1-propyl-1H-imidazol-3-ium iodide,
1-butyl-4-(3-methoxy-3-oxopropyl)-3-methyl-1H-imidazol-3-ium iodide,
1-butyl-3-ethyl-4-(3-methoxy-3-oxopropyl)-1H-imidazol-3-ium iodide,
1-butyl-4-(3-methoxy-3-oxopropyl)-3-propyl-1H-imidazol-3-ium iodide,
1,3-dibutyl-4-(3-methoxy-3-oxopropyl)-1H-imidazol-3-ium iodide,
1-butyl-4-(3-methoxy-3-oxopropyl)-3-pentyl-1H-imidazol-3-ium iodide,
1-butyl-3-hexyl-4-(3-methoxy-3-oxopropyl)-1H-imidazol-3-ium iodide,
4-(3-methoxy-3-oxopropyl)-3-methyl-1-pentyl-1H-imidazol-3-ium iodide,
3-ethyl-4-(3-methoxy-3-oxopropyl)-1-pentyl-1H-imidazol-3-ium iodide,
4-(3-methoxy-3-oxopropyl)-1-pentyl-3-propyl-1H-imidazol-3-ium iodide,
3-butyl-4-(3-methoxy-3-oxopropyl)-1-pentyl-1H-imidazol-3-ium iodide,
4-(3-methoxy-3-oxopropyl)-1,3-dipentyl-1H-imidazol-3-ium iodide,
3-hexyl-4-(3-methoxy-3-oxopropyl)-1-pentyl-1H-imidazol-3-ium iodide,
1-hexyl-4-(3-methoxy-3-oxopropyl)-3-methyl-1H-imidazol-3-ium iodide,
3-ethyl-1-hexyl-4-(3-methoxy-3-oxopropyl)-1H-imidazol-3-ium iodide,
1-hexyl-4-(3-methoxy-3-oxopropyl)-3-propyl-1H-imidazol-3-ium iodide,
3-butyl-1-hexyl-4-(3-methoxy-3-oxopropyl)-1H-imidazol-3-ium iodide,
1-hexyl-4-(3-methoxy-3-oxopropyl)-3-pentyl-1H-imidazol-3-ium iodide,
1,3-dihexyl-4-(3-methoxy-3-oxopropyl)-1H-imidazol-3-ium iodide,
3-ethyl-4-(3-methoxy-3-oxopropyl)-1-methyl-1H-imidazol-3-ium bromide,
4-(3-methoxy-3-oxopropyl)-1-methyl-3-propyl-1H-imidazol-3-ium bromide,
4-(3-methoxy-3-oxopropyl)-1-methyl-3-pentyl-1H-imidazol-3-ium bromide,
3-hexyl-4-(3-methoxy-3-oxopropyl)-1-methyl-1H-imidazol-3-ium bromide,
1-ethyl-4-(3-methoxy-3-oxopropyl)-3-methyl-1H-imidazol-3-ium bromide,
1,3-diethyl-4-(3-methoxy-3-oxopropyl)-1H-imidazol-3-ium bromide,
1-ethyl-4-(3-methoxy-3-oxopropyl)-3-propyl-1H-imidazol-3-ium bromide,
1-ethyl-4-(3-methoxy-3-oxopropyl)-3-pentyl-1H-imidazol-3-ium bromide,
1-ethyl-3-hexyl-4-(3-methoxy-3-oxopropyl)-1H-imidazol-3-ium bromide,
4-(3-methoxy-3-oxopropyl)-3-methyl-1-propyl-1H-imidazol-3-ium bromide,
3-ethyl-4-(3-methoxy-3-oxopropyl)-1-propyl-1H-imidazol-3-ium bromide,
4-(3-methoxy-3-oxopropyl)-1,3-dipropyl-1H-imidazol-3-ium bromide,
3-butyl-4-(3-methoxy-3-oxopropyl)-1-propyl-1H-imidazol-3-ium bromide,
4-(3-methoxy-3-oxopropyl)-3-pentyl-1-propyl-1H-imidazol-3-ium bromide,
3-hexyl-4-(3-methoxy-3-oxopropyl)-1-propyl-1H-imidazol-3-ium bromide,
1-butyl-4-(3-methoxy-3-oxopropyl)-3-propyl-1H-imidazol-3-ium bromide,
1,3-dibutyl-4-(3-methoxy-3-oxopropyl)-1H-imidazol-3-ium bromide,
1-butyl-4-(3-methoxy-3-oxopropyl)-3-pentyl-1H-imidazol-3-ium bromide,
1-butyl-3-hexyl-4-(3-methoxy-3-oxopropyl)-1H-imidazol-3-ium bromide,
4-(3-methoxy-3-oxopropyl)-3-methyl-1-pentyl-1H-imidazol-3-ium bromide,
3-ethyl-4-(3-methoxy-3-oxopropyl)-1-pentyl-1H-imidazol-3-ium bromide,
4-(3-methoxy-3-oxopropyl)-1-pentyl-3-propyl-1H-imidazol-3-ium bromide,
3-butyl-4-(3-methoxy-3-oxopropyl)-1-pentyl-1H-imidazol-3-ium bromide,
4-(3-methoxy-3-oxopropyl)-1,3-dipentyl-1H-imidazol-3-ium bromide,
3-hexyl-4-(3-methoxy-3-oxopropyl)-1-pentyl-1H-imidazol-3-ium bromide,
1-hexyl-4-(3-methoxy-3-oxopropyl)-3-methyl-1H-imidazol-3-ium bromide,
3-ethyl-1-hexyl-4-(3-methoxy-3-oxopropyl)-1H-imidazol-3-ium bromide,
1-hexyl-4-(3-methoxy-3-oxopropyl)-3-propyl-1H-imidazol-3-ium bromide,
3-butyl-1-hexyl-4-(3-methoxy-3-oxopropyl)-1H-imidazol-3-ium bromide,
1-hexyl-4-(3-methoxy-3-oxopropyl)-3-pentyl-1H-imidazol-3-ium bromide,
1,3-dihexyl-4-(3-methoxy-3-oxopropyl)-1H-imidazol-3-ium bromide, 4-(3-methoxy-3-oxopropyl)-1,2,3-trimethyl-1H-imidazol-3-ium iodide,
3-ethyl-4-(3-methoxy-3-oxopropyl)-1,2-dimethyl-1H-imidazol-3-ium iodide,
4-(3-methoxy-3-oxopropyl)-1,2-dimethyl-3-propyl-1H-imidazol-3-ium iodide,
3-butyl-4-(3-methoxy-3-oxopropyl)-1,2-dimethyl-1H-imidazol-3-ium iodide,
4-(3-methoxy-3-oxopropyl)-1,2-dimethyl-3-pentyl-1H-imidazol-3-ium iodide,
3-hexyl-4-(3-methoxy-3-oxopropyl)-1,2-dimethyl-1H-imidazol-3-ium iodide,
1,3-diethyl-4-(3-methoxy-3-oxopropyl)-2-methyl-1H-imidazol-3-ium iodide,
4-(3-methoxy-3-oxopropyl)-2-methyl-1,3-dipropyl-1H-imidazol-3-ium iodide,
1,3-dibutyl-4-(3-methoxy-3-oxopropyl)-2-methyl-1H-imidazol-3-ium iodide,
4-(3-methoxy-3-oxopropyl)-2-methyl-1,3-dipentyl-1H-imidazol-3-ium iodide,
1,3-dihexyl-4-(3-methoxy-3-oxopropyl)-2-methyl-1H-imidazol-3-ium iodide,
1-ethyl-3-hexyl-4-(3-methoxy-3-oxopropyl)-2-methyl-1H-imidazol-3-ium iodide,
4-(3-methoxy-3-oxopropyl)-1-methyl-3-propyl-1H-imidazol-3-ium bromide,
4-(3-methoxy-3-oxopropyl)-1,2,3-trimethyl-1H-imidazol-3-ium bromide,
3-ethyl-4-(3-methoxy-3-oxopropyl)-1,2-dimethyl-1H-imidazol-3-ium bromide,
4-(3-methoxy-3-oxopropyl)-1,2-dimethyl-3-propyl-1H-imidazol-3-ium bromide,
3-butyl-4-(3-methoxy-3-oxopropyl)-1,2-dimethyl-1H-imidazol-3-ium bromide,
4-(3-methoxy-3-oxopropyl)-1,2-dimethyl-3-pentyl-1H-imidazol-3-ium bromide,
3-hexyl-4-(3-methoxy-3-oxopropyl)-1,2-dimethyl-1H-imidazol-3-ium bromide,
1,3-diethyl-4-(3-methoxy-3-oxopropyl)-2-methyl-1H-imidazol-3-ium bromide,
4-(3-methoxy-3-oxopropyl)-2-methyl-1,3-dipropyl-1H-imidazol-3-ium bromide,
1,3-dibutyl-4-(3-methoxy-3-oxopropyl)-2-methyl-1H-imidazol-3-ium bromide,
4-(3-methoxy-3-oxopropyl)-2-methyl-1,3-dipentyl-1H-imidazol-3-ium bromide, and
1-ethyl-3-hexyl-4-(3-methoxy-3-oxopropyl)-2-methyl-1H-imidazol-3-ium iodide.

DETAILED DESCRIPTION

Figure 1:
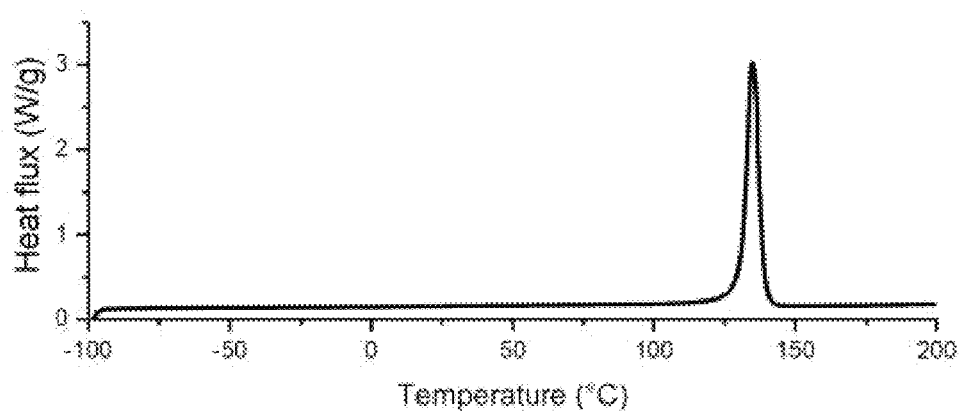
FIG. 1 is a graph of the results of the calorimetric analysis of the compound 3a from example 1.

The present invention is illustrated by the following exemplary embodiments, to which, however, it is not limited.

EXAMPLES

The following starting materials were used in the examples:
N-butylbenzimidazole (Merck);
Urocanic acid; anhydrous methanol; sodium sulfuret; concentrated sulfuric acid; sodium carbonate; cyclohexane; 10% palladium-on-charcoal (10% Pd/C); potassium carbonate; methyl iodide; ethyl iodide; potassium iodide; 1-bromopropane; 1-iodopropane; 1-iodobutane; 1-iodopentane; 1-iodohexane; molecular iodine; guanidinium thiocyanate (Sigma-Aldrich);
Ethyl acetate; acetone, dichloromethane (VWR);
3-Methoxypropionitrile (Alfa Aesar);
1,3-Dimethylimidazolium iodide (DMII) (Solvionic).

Example 1

Synthesis of 4-(3-methoxy-3-oxopropyl)-1,3-dimethyl-1H-imidazol-3-ium Iodide (Compound 3a)

In this example, the synthesis has been carried out of a compound of formula (I) in which the R$^1$, R$^2$ and R$^4$ radicals are identical and represent a methyl radical, R$^3$ representing a hydrogen atom:

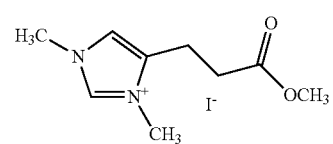

1) First Stage: Synthesis of the Methyl Ester of Urocanic Acid (Compound 1)

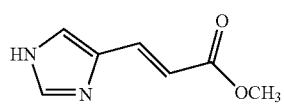

11.5 ml of concentrated sulfuric acid were added to a solution of urocanic acid (20 g, 145 mmol) and sodium sulfurte (2.8 g) in anhydrous methanol (215 ml). After stirring at 70° C. overnight, the reaction mixture was cooled to ambient temperature and filtered. The solvent was subsequently removed under reduced pressure and water was added (1 ml). The solution thus obtained was neutralized to neutral pH by addition of a saturated sodium carbonate solution. The solution was subsequently extracted 4 times with ethyl acetate and then the organic phases were combined and dried over sodium sulfurte. The solvent was subsequently removed under reduced pressure. After dissolution of the precipitate with a minimum amount of ethyl acetate, 300 ml of cyclohexane were added. After filtration, the expected compound 1 was obtained in the form of a white solid (20 g, yield 92%).

Melting point: 74-76° C.

$^1$H NMR (d$_6$-DMSO 300 MHz): δ (ppm) 7.80 (s, 1H, NCHN); 7.55 (d, 1H, J=15.6 Hz, CH═CH); 7.51 (s, 1H, NCH); 6.40 (d, 1H, J=15.6 Hz, CH═CH); 3.65 (s, 3H, OCH$_3$)

$^{13}$C NMR (d$_6$-DMSO 75 MHz): δ (ppm) 167.7 (CO); 138.2 (NCHN); 136.3 (CH═); 134.7 (Cq); 123.9 (CH═); 111.1 (NCH); 51.5 (OCH$_3$).

Molar mass calculated for C$_7$H$_8$N$_2$O$_2$Na$^+$: 175 g·mol$^{-1}$; found 175 g·mol$^{-1}$.

2) Second Stage: Synthesis of Methyl 3-(1H-imidazol-4-yl)propanoate Compound 2)

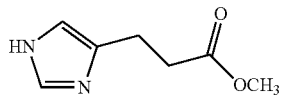

2

1.5 g of 10% Pd/C were added to a solution of 20 g (133 mmol) of the methyl ester of urocanic acid (compound 1a obtained in the preceding stage 1)) in 150 ml of methanol under molecular hydrogen pressure. After hydrogenating at ambient temperature for 14 hours, the reaction medium was filtered through celite. The filtrate was subsequently evaporated under reduced pressure to result in 19.6 g of the expected compound 2 (yield 95%) in the form of a slightly orange syrup.

$^1$H NMR (CDCl$_3$, 300 MHz): δ (ppm) 9.65 (s, 1H, NCHN); 7.55 (s, 1H, NCH); 6.77 (s, 1H, NH); 3.61 (s, 3H, OCH$_3$); 2.90 (t, 2H, J=7.5 Hz, CH$_2$); 2.63 (t, 2H, J=7.5 Hz, CH$_2$)

$^{13}$C NMR (CDCl$_3$, 75 MHz): δ (ppm) 173.6 (CO); 135.6 (Cq); 134.7 (NCHN); 116.7 (NCH); 51.6 (OCH$_3$); 33.8 (CH$_2$); 22.1 (CH$_2$).

Molar mass calculated for C$_7$H$_{10}$N$_2$O$_2$Na$^+$: 177 g/mol; found 177 g/mol.

3) Third Stage: Synthesis of 4-(3-Methoxy-3-Oxopropyl)-1,3-Diimethyl-1H-Imidazol-3-Ium Iodide (Compound 3a)

5 g of the compound 2 obtained above in the preceding stage (32.4 mmol), 9 g of potassium carbonate (65 mmol) and 8.1 ml of methyl iodide were added to 100 ml of acetone. The reaction mixture was maintained at 70° C. with stirring for 1 hour. After cooling to ambient temperature, the reaction mixture was filtered and the solvent was removed under reduced pressure. The precipitate formed was dissolved in dichloromethane, the mixture was then filtered and the solvent was removed under reduced pressure. The reaction mixture was subsequently triturated in cyclohexane and the solid was filtered to result in 8.6 g of expected compound 3a in the form of a white solid (yield 86%).

Melting point: 134.7° C.

$^1$H NMR (CDCl$_3$, 300 MHz): δ (ppm) 9.76 (s, 1H, NCHN); 7.35 (s, 1H, NCH); 3.99; 3.94 (s, 6H, 2×NCH$_3$); 3.64 (s, 3H, OCH$_3$); 2.95 (dd, 2H, J=6.5 Hz, J=7.5 Hz, CH$_2$); 2.73 (t, 2H, J=7.0 Hz, CH$_2$)

$^{13}$C NMR (CDCl$_3$, 75 MHz): δ (ppm) 171.7 (CO); 136.7 (NCHN); 134.5 (Cq); 120.7 (NCH); 52.2 (OCH$_3$); 36.9; 34.4 (2×NCH$_3$); 31.8 (CH$_2$); 18.9 (CH$_2$).

Molar mass calculated for C$_9$H$_{15}$N$_2$O$_2^+$: 183 g/mol; found 183 g/mol.

A calorimetric analysis under air of the compound 3a was carried out using a calorimeter sold under the trade name DSC204 F1 by Netzsch.

A thermogravimetric analysis under air of the compound 3a was also carried out after storage exposed to the air for 3 weeks.

By way of comparison, a thermogravimetric analysis of an imidazolium iodide not coming within the invention, namely 1,3-dimethylimidazolium iodide (DMII), was also carried out.

Figure 2:
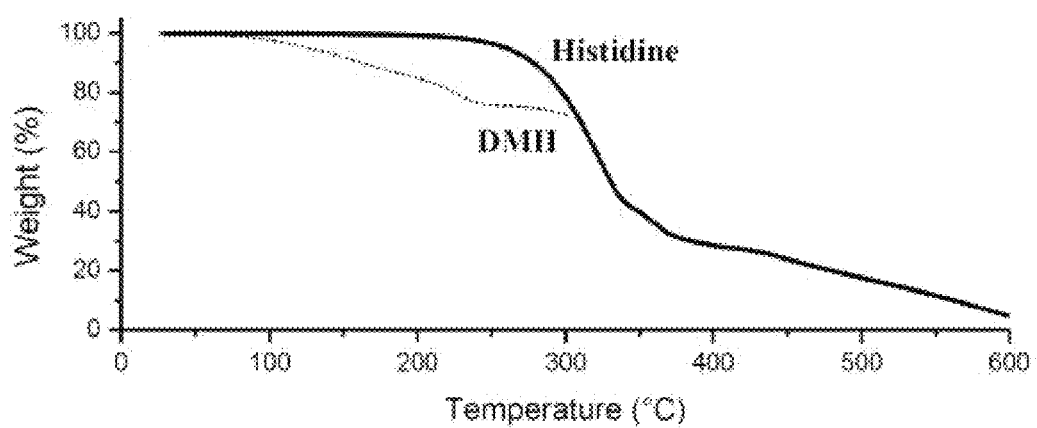
FIG. 2 is a graph of the results of the thermogravimetric analysis for the compound 3a (continuous line) in comparison with the DMII (noncontinuous line) from example 1.

The results obtained are given in the appended FIGS. 1 and 2. FIG. 1 gives the results of the calorimetric analysis of the compound 3a. In this figure, the heat flux (in W/g) is a function of the temperature (in ° C.). FIG. 2 gives the results of the thermogravimetric analysis for the compound 3a (continuous line) in comparison with the DMII (noncontinuous line).

The results of the thermogravimetric analysis under air show that the compound 3a is particularly stable up to a temperature of 300° C., thus well beyond the conditions of accelerated aging of thin film photovoltaic cells laid down by the standard IEC 61646, which is 1000 hours at 60° C./100 mW·cm$^{-2}$ under illumination and 1000 hours at 85° C. in the dark. In comparison, DMII allows a loss in weight of the order of 30% originating from the water captured as a result of its hygroscopicity. In contrast, even after storage of the compound 3a exposed to the air for 3 weeks, this compound does not exhibit any hygroscopicity nature, which opens it to use and to storage outside glove boxes or dry rooms.

Example 2

Synthesis of 4-(3-methoxy-3-oxopropyl)-1,3-diethyl-1H-imidazol-3-ium Iodide (Compound 3b)

In this example, the synthesis was carried out of a compound of formula (I) in which R$^1$ is a methyl radical and the R$^2$ and R$^4$ radicals are identical and represent an ethyl radical, R$^3$ representing a hydrogen atom:

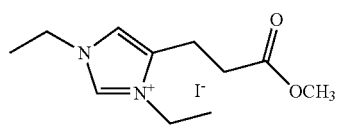

3b 5 g of the compound 2 obtained above in stage 2) of example 1 (324 mmol), 9 g of potassium carbonate (65 mmol) and 7.8 ml of ethyl iodide were added to 100 ml of acetone. The reaction mixture was maintained at 70° C. with stirring overnight. After cooling to ambient temperature, the reaction mixture was filtered and the solvent was removed under reduced pressure. The precipitate formed was dissolved in dichloromethane, the mixture was then filtered and the solvent was removed under reduced pressure. The reaction mixture was subsequently triturated in cyclohexane and the solid was filtered off to result in 9.5 g of the expected compound 3b in the form of a light yellow solid (yield 86%).

Melting point: 111° C.

$^1$H NMR (CDCl$_3$, 300 MHz): δ (ppm) 9.86 (s, 1H, NCHN); 7.41 (s, 1H, NCH); 4.30 (dd, 2H, J=7.3 Hz, J=14.7 Hz, NCH$_2$); 4.24 (dd, 2H, J=7.3 Hz, J=14.7 Hz, NCH$_2$); 3.61 (s, 3H, OCH$_3$); 2.92 (m, 2H, CH$_2$); 2.72 (t, 2H, J=6.7 Hz, CH$_2$); 1.52 (m, 6H, 2×CH$_3$)

$^{13}$C NMR (CDCl$_3$, 75 MHz): δ (ppm) 171.8 (CO); 135.2 (NCHN); 133.8 (Cq); 119.2 (NCH); 52.1 (OCH$_3$); 45.2; 42.6 (2×NCH$_2$); 31.8 (CH$_2$); 18.9 (CH$_2$); 15.6; 15.5 (2×CH$_3$)

Molar mass calculated for C$_{11}$H$_{19}$N$_2$O$_2{}^+$: 211.1447 g/mol; found 211.1446 g/mol.

Example 3

Synthesis of 4-(3-methoxy-3-oxopropyl)-1,3-dipropyl-1H-imidazol-3-ium Iodide (Compound 3c)

In this example, the synthesis was carried out of a compound of formula (I) in which R$^1$ is a methyl radical and the R$^2$ and R$^4$ radicals are identical and represent a propyl radical, R$^3$ representing a hydrogen atom:

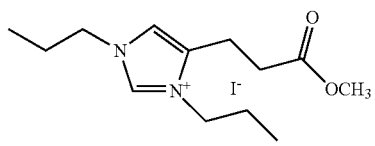

4.6 g of a compound 2 obtained above in stage 2) of example 1 (297 mmol), 8.2 g of potassium carbonate (59.4 mmol) and 8.7 ml of 1-iodopropane were added to 100 ml of acetone. The reaction mixture was maintained at 70° C. under stirring for 3 days. After cooling to ambient temperature, the reaction mixture was filtered and the solvent was removed under reduced pressure. After purifying through silica gel (methanol/ethyl acetate 10/90), 3.8 g of the compound 3c are obtained in the form of a viscous orange liquid (yield 25%).

$^1$H NMR (d$_6$-DMSO, 300 MHz): δ (ppm) 9.25 (s, 1H, NCHN); 7.66 (s, 1H, NCH); 4.13 (m, 4H, 2×NCH$_2$); 3.63 (s, 3H, OCH$_3$); 2.93 (m, 2H, CH$_2$); 2.75 (m, 2H, CH$_2$); 1.81 (m, 4H, 2×CH$_2$); 0.88 (m, 6H, 2×CH$_3$)

$^{13}$C NMR (d$_6$-DMSO, 75 MHz): δ (ppm) 172.3 (CO); 136.0 (NCHN); 134.2 (Cq); 119.6 (NCH); 52.1 (OCH$_3$); 50.8; 48.2 (2×NCH$_2$); 31.5; 23.1; 22.8; 18.8 (4×CH$_2$); 10.9; 10.8 (2×CH$_3$)

Molar mass calculated for C$_{13}$H$_{23}$N$_2$O$_2{}^+$: 239.1760 g/mol; found 239.1760 g/mol.

Example 4

Synthesis of 4-(3-methoxy-3-oxopropyl)-1,3-dibutyl-1H-imidazol-3-ium Iodide (Compound 3d)

In this example, the synthesis was carried out of a compound of formula (I) in which R$^1$ is a methyl radical and the R$^2$ and R$^4$ radicals are identical and represent a butyl radical, R$^3$ representing a hydrogen atom:

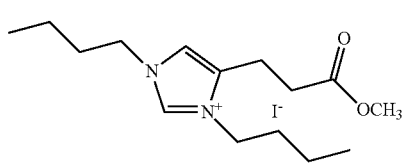

5 g of the compound 2 obtained above in stage 2) of example 1 (324 mmol), 8.9 g of potassium carbonate (65 mmol) and 11.1 ml of 1-iodobutane were added to 100 ml of acetone. The reaction mixture was maintained at 70° C. with stirring for 3 days. After cooling to ambient temperature, the reaction mixture was filtered and the solvent was removed under reduced pressure. After purification through silica gel (methanol/ethyl acetate 10/90), 5.8 g of the compound 3d are obtained in the form of a viscous orange liquid (yield 45%).

$^1$H NMR (d$_6$-DMSO, 300 MHz): δ (ppm) 9.35 (s, 1H, NCHN); 7.71 (s, 1H, NCH); 4.17 (m, 4H, 2×NCH$_2$); 3.61 (s, 3H, OCH$_3$); 2.93 (t, 2H, J=7.2 Hz, CH$_2$); 2.74 (t, 2H, J=7.2 Hz, CH$_2$); 1.76 (m, 4H, 2×CH$_2$); 1.26 (m, 4H, 2×CH$_2$); 0.88 (m, 6H, 2×CH$_3$)

$^{13}$C NMR (d$_6$-DMSO, 75 MHz): δ (ppm) 172.3 (CO); 135.9 (NCHN); 134.0 (Cq); 119.7 (NCH); 52.2 (OCH$_3$); 49.0; 46.6 (2×NCH$_2$); 31.7; 31.6; 31.3; 19.4; 19.2; 18.9 (6×CH$_2$); 13.8, 13.7 (2×CH$_3$)

Molar mass calculated for C$_{15}$H$_{27}$N$_2$O$_2{}^+$: 267.2073; found 267.2081.

Example 5

Synthesis of 4-(3-methoxy-3-oxopropyl)-1,3-dipentyl-1H-imidazol-3-ium Iodide (Compound 3e)

In this example, the synthesis was carried out of a compound of formula (I) in which R$^1$ is a methyl radical and the R$^2$ and R$^4$ radicals are identical and represent a pentyl radical, R$^3$ representing a hydrogen atom:

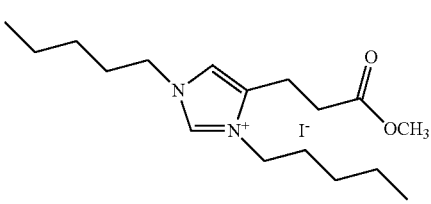

5 g of the compound 2 obtained above in stage 2) of example 1 (324 mmol), 8.9 g of potassium carbonate (65 mmol) and 11.1 ml of 1-iodopentane were added to 100 ml of acetone. The reaction mixture was maintained at 70° C. with stirring for 3 days. After cooling to ambient temperature, the reaction mixture was filtered and the solvent was removed under reduced pressure. After purification through silica gel (methanol/ethyl acetate 10/90), 10.6 g of the compound 3e are obtained in the form of a viscous orange liquid (yield 79%).

$^1$H NMR (d$_6$-DMSO, 300 MHz): δ (ppm) 9.25 (s, 1H, NCHN); 7.66 (s, 1H, NCH); 4.15 (t, 4H, J=7.4 Hz, 2×NCH$_2$); 3.63 (s, 3H, OCH$_3$); 2.93 (t, 2H, J=7.2 Hz, CH$_2$); 2.76 (t, 2H, J=7.2 Hz, CH$_2$); 1.79 (m, 4H, 2×CH$_2$); 1.29 (m, 8H, 4×CH$_2$); 0.88 (m, 6H, 2×CH$_3$)

$^{13}$C NMR (d$_6$-DMSO, 75 MHz): δ (ppm) 172.3 (CO); 136.0 (NCHN); 134.1 (Cq); 119.6 (NCH); 52.1 (OCH$_3$); 49.3; 46.7 (2×NCH$_2$); 31.5; 29.3; 29.0; 28.2; 28.0; 22.0; 21.9, 18.8 (8×CH$_2$); 14. (2×CH$_3$)

Molar mass calculated for C$_{17}$H$_{31}$N$_2$O$_2$$^+$: 295.2386 g/mol; found 295.2382 g/mol.

Example 6

Synthesis of 4-(3-methoxy-3-oxopropyl)-1,3-dihexyl-1H-imidazol-3-ium Iodide (Compound 3f)

In this example, the synthesis was carried out of a compound of formula (I) in which R$^1$ is a methyl radical and R$^2$ and R$^4$ radicals are identical and represent a hexyl radical, R$^3$ representing a hydrogen atom:

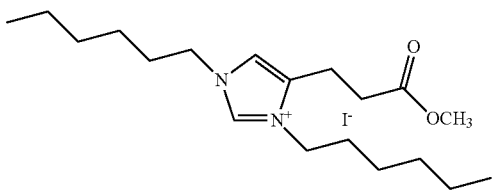

3f 5 g of the compound 2 obtained above in stage 2) of example 1 (324 mmol), 8.9 g of potassium carbonate (65 mmol) and 14.3 ml of 1-iodohexane were added to 100 ml of acetone. The reaction mixture was maintained at 70° C. with stirring for 3 days. After cooling to ambient temperature, the reaction mixture was filtered and the solvent was removed under reduced pressure. After purification through silica gel (methanol/ethyl acetate 10/90), 11.6 g of the compound 3f are obtained in the form of a viscous orange liquid (yield 79%).

$^1$H NMR (d$_6$-DMSO, 300 MHz): δ (ppm) 9.31 (s, 1H, NCHN); 7.69 (s, 1H, NCH); 4.16 (t, 4H, J=7.2 Hz, 2×NCH$_2$); 3.62 (s, 3H, OCH$_3$); 2.93 (t, 2H, J=7.2 Hz, CH$_2$); 2.76 (t, 2H, J=7.2 Hz, CH$_2$); 1.78 (m, 4H, 2×CH$_2$); 1.29 (m, 12H, 6×CH$_2$); 0.85 (m, 6H, 2×CH$_3$)

$^{13}$C NMR (d$_6$-DMSO, 75 MHz): δ (ppm) 172.3 (CO); 136.0 (NCHN); 134.1 (Cq); 119.6 (NCH); 52.1 (OCH$_3$); 49.3; 46.8 (2×NCH$_2$); 31.5; 31.0; 30.9; 29.6; 29.3; 25.7; 25.5; 22.3; 18.9 (10×CH$_2$); 14.2 (2×CH$_3$)

Molar mass calculated for C$_{19}$H$_{35}$N$_2$O$_2$$^+$: 323.2699 g/mol; found 323.2691 g/mol.

Example 7

Synthesis of 4-(3-ethoxy-3-oxopropyl)-1,3-dimethyl-1H-imidazol-3-ium Iodide (Compound 6)

In this example, the synthesis was carried out of a compound of formula (I) in which the R$^2$ and R$^4$ radicals are identical and represent a methyl radical and R$^1$ represents an ethyl radical, R$^3$ representing a hydrogen atom:

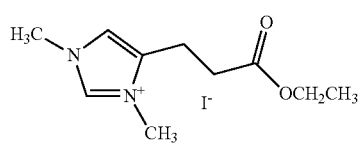

6

1) First Stage: Synthesis of the Ethyl Ester of Urocanic Acid (Compound 4)

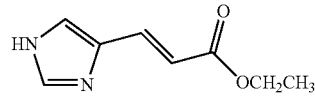

4

14.3 ml of concentrated sulfuric acid were added to a solution of urocanic acid (25 g, 181 mmol) and sodium sulfurte (3.5 g) in anhydrous ethanol (165 ml). After stirring at 70° C. overnight, the reaction mixture was cooled to ambient temperature and filtered. The solvent was subsequently removed under reduced pressure and water was added (1 ml). The solution thus obtained was neutralized to neutral pH by addition of a saturated sodium carbonate solution. The solution was subsequently extracted 4 times with ethyl acetate and then the organic phases were combined and dried over sodium sulfurte. The solvent was subsequently removed under reduced pressure. After dissolution of the precipitate with a minimum amount of ethyl acetate, 300 ml of cyclohexane were added. After filtration, the expected compound 4 was obtained in the form of a white solid (29 g, yield 96%).

Melting point: 81-82° C.

$^1$H NMR (d$_6$-DMSO, 400 MHz): δ (ppm) 7.78 (s, 1H, NCHN); 7.54 (s, 1H, N=CH); 7.53 (d, 1H, J$_{a,b}$=15.6 Hz, H$_a$ CH=); 6.33 (d, 1H, J$_{a,b}$=15.6 Hz, H$_b$ CH=); 4.15 (q, 2H, J$_{CH2,CH3}$=7.1 Hz, CH$_2$); 1.23 (t, 3H, J$_{CH2,CH3}$=7.1 Hz, CH$_3$)

$^{13}$C NMR (d$_6$-DMSO, 100 MHz): δ (ppm) 167.0 (CO); 138.2 (NCH=, CH=), 114.0 (CH=, NCH=); 60.0 (CH$_2$); 14.7 (CH$_3$)

Molar mass calculated for C$_8$H$_{12}$N$_2$O$_2$Na: 191.0796 g/mol; found 191.0800 g/mol.

2) Second Stage: Synthesis of Ethyl 3-(1H-imidazol-4-yl)propanoate Compound 5)

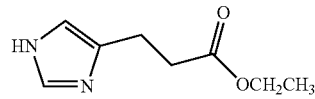

5

1.8 g of 10% Pd/C were added to a solution of 25 g (150 mmol) of ethyl ester of urocanic acid (compound 4 obtained in the preceding stage 1)) in 150 ml of methanol under molecular hydrogen pressure. After hydrogenating at ambient temperature for 14 hours, the reaction medium was filtered through celite. The filtrate was subsequently evaporated under reduced pressure to result in 23 g of the expected compound 5 (yield 91%) in the form of a slightly orange syrup.

$^1$H NMR (d$_6$-DMSO, 400 MHz): δ (ppm) 7.55 (s, 1H, NCHN); 6.78 (s, 1H, N=CH); 4.04 (q, 2H, J$_{CH2,CH3}$=7.2 Hz, CH$_2$CH$_3$); 2.78 (t, 2H, J$_{CH2,CH2}$=7.8 Hz, CH$_2$CH$_2$); 2.59 (t, 2H, J$_{CH2,CH2}$=7.8 Hz, CH$_2$); 1.15 (t, 3H, J$_{CH2,CH3}$=7.2 Hz, CH$_2$CH$_3$)

$^{13}$C NMR (d$_6$-DMSO, 100 MHz): δ (ppm) 172.7 (CO); 136.1 (Cq); 135.0 (CH=); 116.5 (CH=); 60.2 (CH$_2$CH$_3$); 33.9 (CH$_2$); 22.6 (CH$_2$); 14.7 (CH$_2$CH$_3$)

Molar mass calculated for C$_8$H$_{10}$N$_2$O$_2$Na: 189.0640 g/mol; found 189.0638 g/mol.

3) Third stage: Synthesis of 4-(3-ethoxy-3-oxopropyl)-1,3-dimethyl-1H-imidazol-3-ium Iodide (Compound 6)

5 g of the compound 5 obtained above in the preceding stage (297 mmol), 8.3 g of potassium carbonate (149 mmol) and 9.2 ml of methyl iodide were added to 100 ml of acetone. The reaction mixture was maintained at 70° C. under stirring overnight. After cooling to ambient temperature, the reaction mixture was filtered and the solvent was removed under reduced pressure. The precipitate formed was dissolved in dichloromethane, the mixture was then filtered and the solvent was removed under reduced pressure. The reaction mixture was subsequently triturated in cyclohexane and the solid was filtered off to result in 6.9 g of the expected compound 6 in the form of a white solid (yield 57%).

$^1$H NMR (d$_6$-DMSO, 400 MHz): δ (ppm) 7.55 (s, 1H, NCHN); 6.78 (s, 1H, N=CH); 4.04 (q, 2H, J$_{CH2,CH3}$=7.2 Hz, CH$_2$CH$_3$); 2.78 (t, 2H, J$_{CH2,CH2}$=7.8 Hz, CH$_2$CH$_2$); 2.59 (t, 2H, J$_{CH2,CH2}$=7.8 Hz, CH$_2$); 1.15 (t, 3H, J$_{CH2,CH3}$=7.2 Hz, CH$_2$CH$_3$)

$^{13}$C NMR (d$_6$-DMSO, 100 MHz): δ (ppm) 171.9 (CO); 136.9 (CH=); 134.4 (Cq); 120.6 (CH=); 60.7 (CH$_2$CH$_3$); 36.2 (NCH$_3$); 33.7 (NCH$_3$); 31.6 (CH$_2$); 18.6 (CH$_2$); 14.5 (CH$_2$CH$_3$)

Molar mass calculated for C$_{10}$H$_{17}$N$_2$O$_2$Na: 197.1290 g/mol; found 197.1289 g/mol.

Example 8

Synthesis of 4-(3-methoxy-3-oxopropyl)-1-methyl-3-propyl-1H-imidazol-3-ium Iodide (Compound 8)

In this example, the synthesis was carried out of a compound of formula (I) in which the R$^1$ and R$^2$ radicals are identical and represent a methyl radical, R$^3$ represents a hydrogen atom and R$^4$ represents a propyl radical:

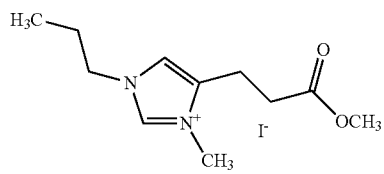

1) First Stage: Synthesis of Methyl 3-(1-propyl-1H-imidazol-4-yl)propanoate Compound 7

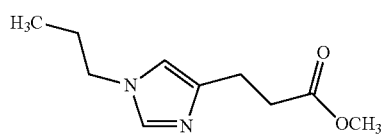

3.9 g (31.9 mmol) of 1-bromopropane were added to a solution of 4.9 g (31.9 mmol) of the compound 2 obtained above in stage 2) of example 1, of 5.3 g (31.9 mmol) of potassium iodide and of 8.8 g (63.9 mmol) of potassium carbonate in 100 ml of acetone. The reaction mixture was maintained at 70° C. under stirring overnight and then filtered. The solvent was removed under reduced pressure. After flash chromatography through silica gel (eluent 100% ethyl acetate and then a methanol/ethyl acetate 5/95 v/v mixture), 1.4 g of the expected compound 7 (yield 23%) was obtained in the form of a colorless syrup.

$^1$H NMR (CDCl$_3$, 300 MHz): δ (ppm) 9.91 (s, 1H, NCHN); 7.40 (s, 1H, NCH); 4.22 (m, 2H, NCH$_2$); 3.64 (s, 3H, OCH$_3$); 2.94 (t, 2H, J=7.2 Hz, CH$_2$); 2.76 (t, 2H, J=6.9 Hz, CH$_2$); 1.94 (m, 2H, CH$_2$CH$_3$); 0.95 (m, 3H, CH$_3$CH$_2$)

$^{13}$C NMR (CDCl$_3$, 75 MHz): δ (ppm) 171.7 (CO); 135.9 (NCHN); 133.9 (Cq); 119.4 (NCH); 52.2 (OCH$_3$); 48.7 (NCH$_2$); 31.8 (CH$_2$); 23.5 (CH$_2$CH$_3$); 19.0 (CH$_2$); 10.8 (CH$_3$CH$_2$).

Molecular mass calculated for C$_{10}$H$_{16}$N$_2$O$_2$Na$^+$: 219 g/mol; found 219 g/mol.

2) Second Stage: Synthesis of 4-(3-methoxy-3-oxopropyl)-1-methyl-3-propyl-1H-imidazol-3-ium Iodide (Compound 8)

A solution of 1.4 g (7.4 mmol) of the compound 7 obtained above in the preceding stage, of 2.0 g (14.9 mmol) of potassium carbonate and of 1.38 ml (223 mmol) of potassium iodide in 100 ml of acetone was maintained at 70° C. under stirring for 2 hours. After cooling to ambient temperature, the reaction mixture was filtered and the solvent was removed under reduced pressure.

After flash chromatography through silica gel (eluent 100% ethyl acetate and then a methanol/ethyl acetate 5/95 v/v mixture), 931 mg of the expected compound 8 were obtained in the form of a slightly orange-colored syrup (yield 37%).

$^1$H NMR (CD$_3$OD, 300 MHz): δ (ppm) 8.95 (s, 1H, NCHN); 7.50 (s, 1H, NCH); 4.18 (t, 2H, J=7.2 Hz, NCH$_2$); 3.90 (s, 3H, NCH$_3$); 3.73 (s, 3H, OCH$_3$); 3.04 (t, 2H, J=7.0 Hz, CH$_2$); 2.83 (t, 2H, J=7.0 Hz, CH$_2$); 1.95 (q, 2H, J=3.9 Hz; CH$_2$CH$_3$); 1.00 (m, 3H, J=7.5 Hz, CH$_3$CH$_2$)

$^{13}$C NMR (CD$_3$OD, 75 MHz): δ (ppm) 172.4 (CO); 135.9 (NCHN); 135.1 (Cq); 119.2 (NCH); 51.1 (OCH$_3$); 50.9 (NCH$_2$); 32.9 (NCH$_3$); 31.0 (CH$_2$); 23.0 (CH$_2$CH$_3$); 18.4 (CH$_2$); 9.6 (CH$_3$CH$_2$).

Molar mass calculated for C$_{11}$H$_{19}$N$_2$O$_2$$^+$: 211 g/mol; found 211 g/mol.

Example 9

Preparation of Dye-Sensitized Photovoltaic Conversion Cells and Studies of their Properties The compound 3a as prepared above was subsequently used in the preparation of a dye-sensitized photovoltaic cell in accordance with the invention (PC1). By way of comparison, a photovoltaic cell not forming part of the invention was also prepared by using DMII as electrolyte salt (PC2).

The general protocol for the preparation of the PC1 and PC2 cells was as follows:

Electrolyte Compositions:

The following electrolyte composition E1 in accordance with the invention was prepared:
Compound 3a: 1 mol/l;
Molecular iodine: 0.15 mol/l;
N-Butylbenzimidazole: 0.5 mol/l;
Guanidinium thiocyanate: 0.1 mol/l;
3-Methoxypropionitrile: q.s.

By way of comparison, an electrolyte composition E2 not forming part of the invention, with the following composition, was prepared:
DMII: 1 mol/l;
Molecular iodine: 0.15 mol/l;
N-Butylbenzimidazole: 0.5 mol/l;
Guanidinium thiocyanate: 0.1 mol/l;
3-Methoxypropionitrile: q.s.

Preparation of the Photoanode:

An 8 µm layer of titanium dioxide nanoparticles (diameter 20 nm) was applied by screen printing to a sheet of glass (20×14 mm) covered beforehand with a 300 nm FTO layer.

A layer of the RuLL'(ANCS)$_2$ complex having a thickness of approximately 2 nm was subsequently deposited on the FTO layer by dip coating.

Counterelectrode

A layer of platinum nanoparticles was deposited on the counterelectrode either by cathode sputtering starting from a Pt target or else by evaporation of a solution of a platinum precursor (drop casting) by carrying out the thermal decomposition at 450° C. under air of one or more drops of a 40 mmol/l solution of $H_2PtCl_6$ in ethanol or alternatively in isopropanol deposited on the surface of the electrode.

Assembling of the Photovoltaic Cells

Photovoltaic cells PC1 in accordance with the invention and PC2 not forming part of the invention were subsequently assembled by using respectively the electrolyte compositions E1 and E2, in the following way:

A conical hole with a diameter of less than 200 µm was made on the counterelectrode by micro-sandblasting, in order to make possible the injection of the electrolyte into the cell. The photoelectrode and the counterelectrode were assembled using a hot-melt polymer seal of the Surlyn® or Bynel® produced and sold by DuPont. The cell was sealed at a temperature of 130° C. for approximately 5 seconds. The electrolyte was injected by capillary action under high vacuum. The external part of the microcone was finally blocked by a glass strip heat-sealed with a polymer of Surlyn® or Bynel® type using a soldering iron tip. The welding was carried out under ultrasound starting from a gallium and indium eutectic in order to obtain an excellent electrical contact.

These different cells were subsequently tested in photovoltaic conversion under AM 1.5 (Air Mass 1.5 Global) illumination of a class-3A solar radiation simulator (Newport) equipped with a 450 W Xenon lamp. The measurements were carried out with an Oriel PVIV 3A station coupled to a Keithley 2420 SourceMeter.

The standard surface area of the electrodes was between 0.16 cm$^2$ and 0.36 cm$^2$ and the incident surface power was 100 mW/cm$^2$.

Figure 3:
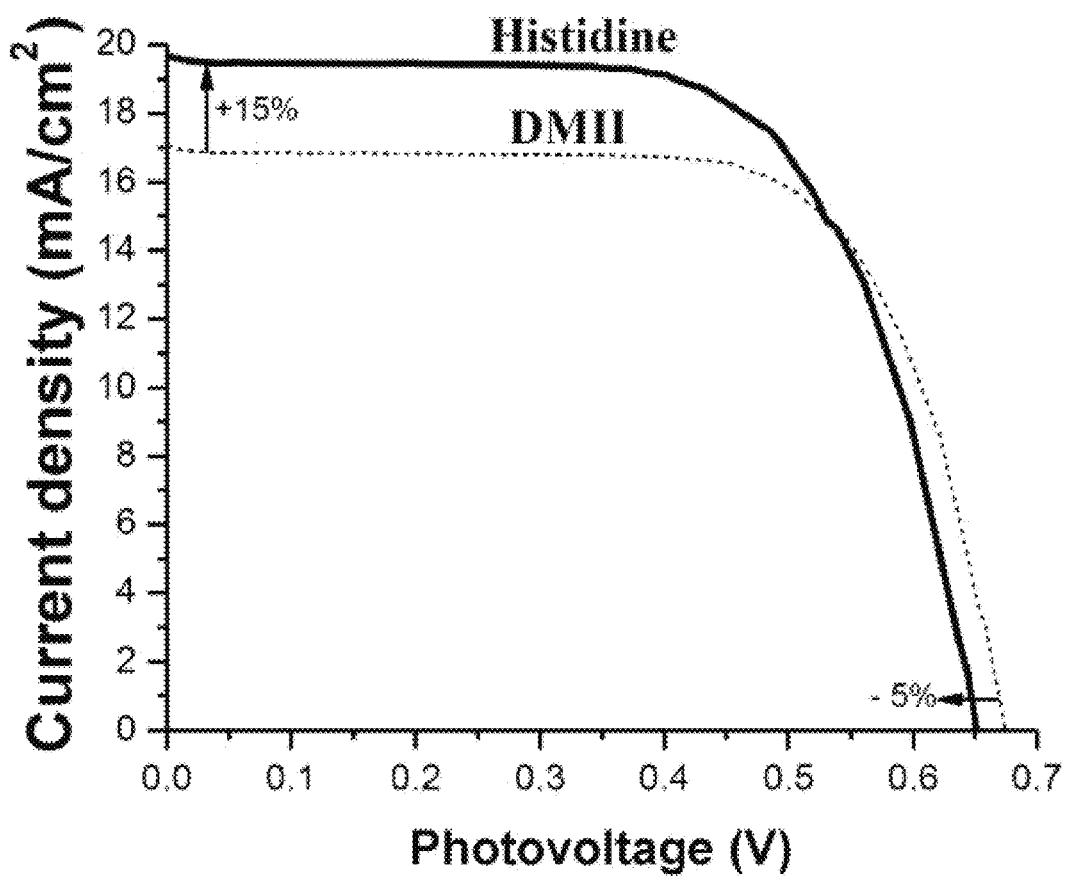
FIG. 3 is a graph comparing the density of the current (in mA/cm$^2$) as a function of the photovoltage (in V) for each of the cells PC1 and PC2 from example 9.

The density of the current (in mA/cm$^2$) as a function of the photovoltage (in V) is compared in the appended FIG. 3 for each of the cells PC1 and PC2. In this figure, the dotted-line curve corresponds to a PC2 cell not forming part of the invention and the continuous-line curve corresponds to a PC1 cell in accordance with the invention.

These results show that, in addition to being a priori more stable chemically and with regard to the Pt interface, the replacement of DMII by the component 3a makes it possible to improve the light/electricity conversion efficiencies, this being because the latter change from 8.0% to 8.5%. The main improvement by virtue of the use of the compound 3a originates from the generation of more photocurrent, the latter changing from 16.9 mA/cm$^2$ to 19.5 mA/cm$^2$ (FIG. 3). On the other hand, the photovoltage changes from 680 mV to 647 mV and the fill factor from 69.3% to 67%. This decrease is largely compensated for by the gain in current, which reaches more than 15%.

The stability of the PC1 and PC2 cells was also studied under conditions of accelerated aging at 70° C., with an incident surface light power at 100 mW/cm$^2$ and in the absence of UV filters.

Figure 4:
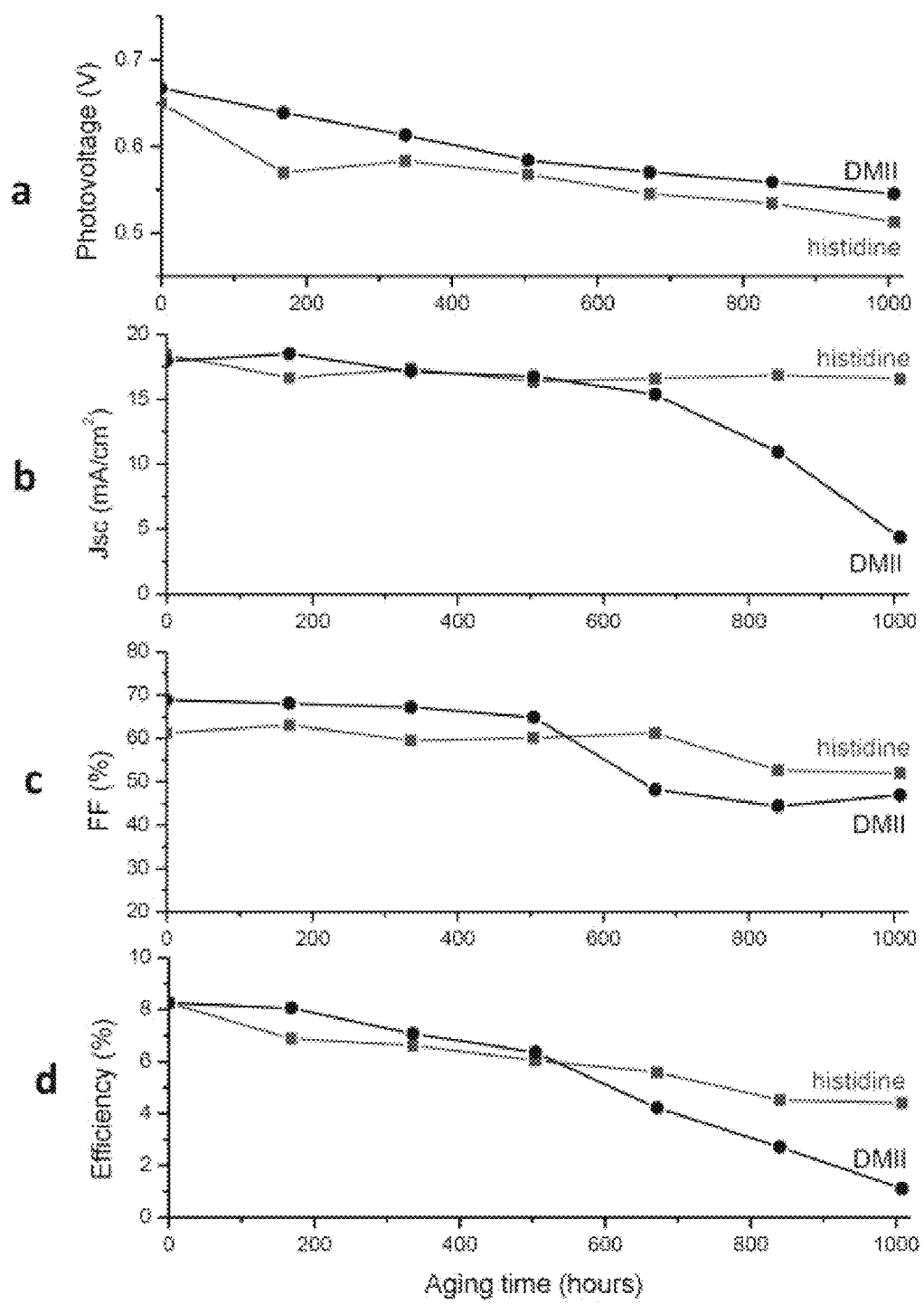
FIG. 4a is a graph of the results of the change in the photovoltage (in V) as a function of the aging time (in hours) from example 9.
FIG. 4b is a graph of the results of the change in the photocurrent (in mA/cm$^2$) as a function of the aging time (in hours) from example 9.
FIG. 4c is a graph of the results of the change in the fill factor (FF, in %) as a function of the aging time (in hours) from example 9.
FIG. 4d is a graph the results of the change in the light/electricity conversion efficiency (in %) as a function of the aging time (in hours) from example 9.

The results obtained are given in the appended FIG. 4. In particular, FIG. 4a gives the results of the change in the photovoltage (in V) as a function of the aging time (in hours), FIG. 4b gives the results of the change in the photocurrent (in mA/cm$^2$) as a function of the aging time (in hours), FIG. 4c gives the results of the change in the fill factor (FF, in %) as a function of the aging time (in hours) and FIG. 4d gives the results of the change in the light/electricity conversion efficiency (in %) as a function of the aging time (in hours). In these figures, the curves with the solid circles correspond to a PC2 cell not forming part of the invention and the curves with the solid squares correspond to a PC1 cell in accordance with the invention.

These results show that the conversion efficiency of the PC2 cell not forming part of the invention falls fairly substantially, in particular after aging for 500 hours. This fall in efficiency is mainly related to a significant loss in the photocurrent and in the fill factor. On the other hand, in the case of a PC1 cell in accordance with the invention, the use of the compound 3a as electrolyte salt in the electrolyte composition makes it possible to maintain the photocurrent at high and very stable values. It also makes it possible to achieve better maintenance of the fill factor under the conditions of accelerated aging. Thus, it is observed that the use of the compound 3a makes it possible to maintain a satisfactory conversion efficiency with a loss of efficiency of only 25% in the case of the compound 3a, against 85% in the case of the DMII, after a duration of aging of 1000 hours.

Figure 5:
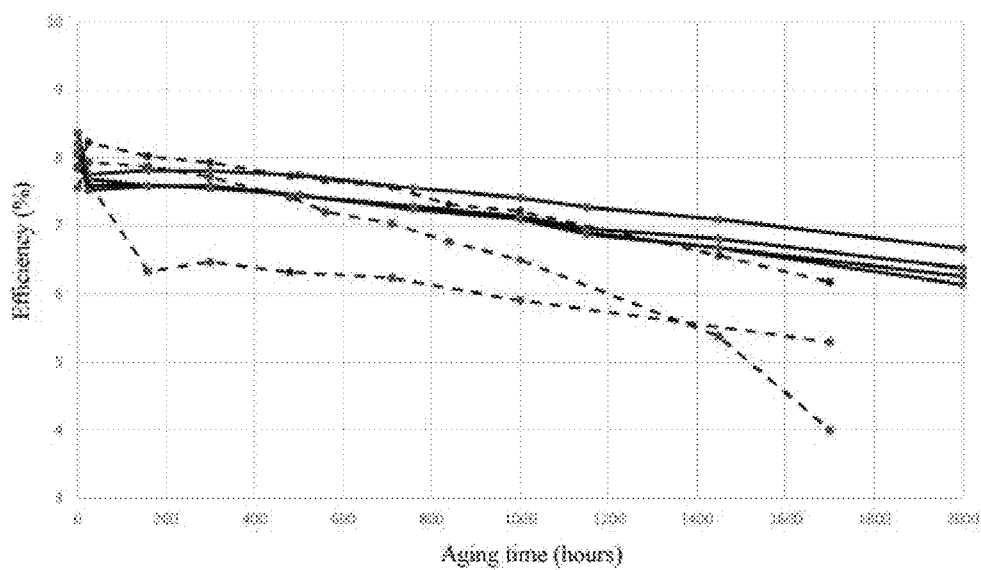
FIG. 5 is a graph of the results of the comparison between a PC1 cell and a PC2 cell under the standard conditions of the IEC 61646 protocol, that is to say at 60° C. under 100 mW·cm$^{-2}$ (UV filter at 340 nm) from example 9.

FIG. 5 gives the results of the comparison between a PC1 cell and a PC2 cell under the standard conditions of the IEC 61646 protocol, that is to say at 60° C. under 100 mW·cm$^{-2}$ (UV filter at 340 nm). In this figure, the light/electricity conversion efficiency (in %) is a function of the aging time (in hours); the solid-line curves correspond to the results of PC1 cells in accordance with the invention and the noncontinuous-line curves correspond to the results of PC2 cells not forming part of the invention. The results given by FIG. 5 also show the superiority of the compound 3a both as regards the efficiencies and the stability over 2000 hours of aging. The four cells assembled with E1 (PC1 cells) have an efficiency retention of the order of 82 to 85%, i.e. greater than the 80% required by the standard IEC 61646 protocol and far beyond the 1000 hours of accelerated aging recommended by the protocol. In contrast, the four cells assembled with E2 (PC2 cells not in accordance with the invention) show a more pronounced decline in the efficiency during aging. One of the four cells had an efficiency of less than 2% after 600 hours (not given) and the other three show a retention of 77%, 66% and 53% after aging for 1700 hours, i.e. values far lower than those observed with the PC1 cells and lower than the bar of 80% of the IEC 61646 protocol.

Figure 6:
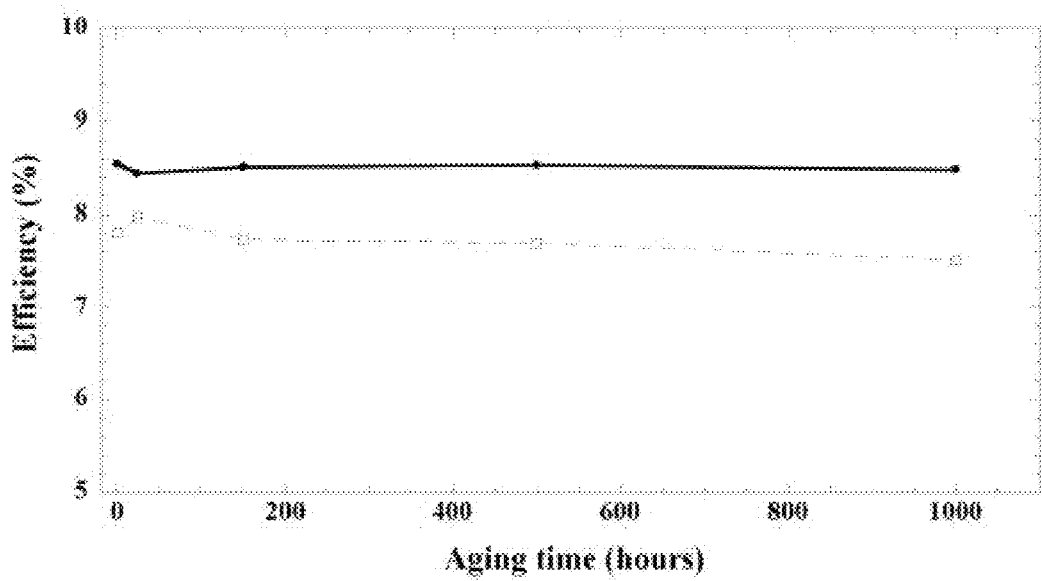
FIG. 6 is a graph of the results obtained with the PC1 and PC2 cells during an aging test at very low temperature (−40° C. in the dark) from example 9.

Finally, FIG. 6 gives the results obtained with the PC1 and PC2 cells during an aging test at very low temperature (−40° C. in the dark). In this figure, the light/electricity conversion efficiency (in %) is a function of the aging time (in hours); the solid-line curve corresponds to the results of PC1 cells in accordance with the invention and the noncontinuous-line curve corresponds to the results of PC2 cells not forming part of the invention. These results show that E1 is also very effective under such conditions of use. The use of this electrolyte shows a retention after 1000 hours of 99.2% against 96.2% for E2. The efficiencies after 1000 hours at −40° C. are 8.48% for E1 and 7.51% for E2.

Example 10

Preparation of Dye-Sensitized Photovoltaic Conversion Cells and Studies of their Properties with Compounds of Formula (I) in Accordance with the Invention of the 3 Series with $R_1=CH_3$, $R_3=H$ and $R_2=R_4=C_nH_{2n+1}$ ($1\leq n\leq 6$) (i.e., the compounds 3a to 3f) and $R_1=C_2H_5$, $R_3=H$ and $R_2=R_4=CH_3$ (Compound 6)

Dye-sensitized photovoltaic cells were prepared using the compounds of the 3 series (compounds 3a to 3f) as prepared in examples 1 to 6 above and also the compound 6 as prepared in example 7, furthermore using, for the composition of the electrolyte, the same ingredients as in electrolyte E1 as prepared in example 9. The preparation of the photoanode and of the counterelectrode and the cell assembling were subsequently carried out in the same way as in example 9 above.

Figure 7:
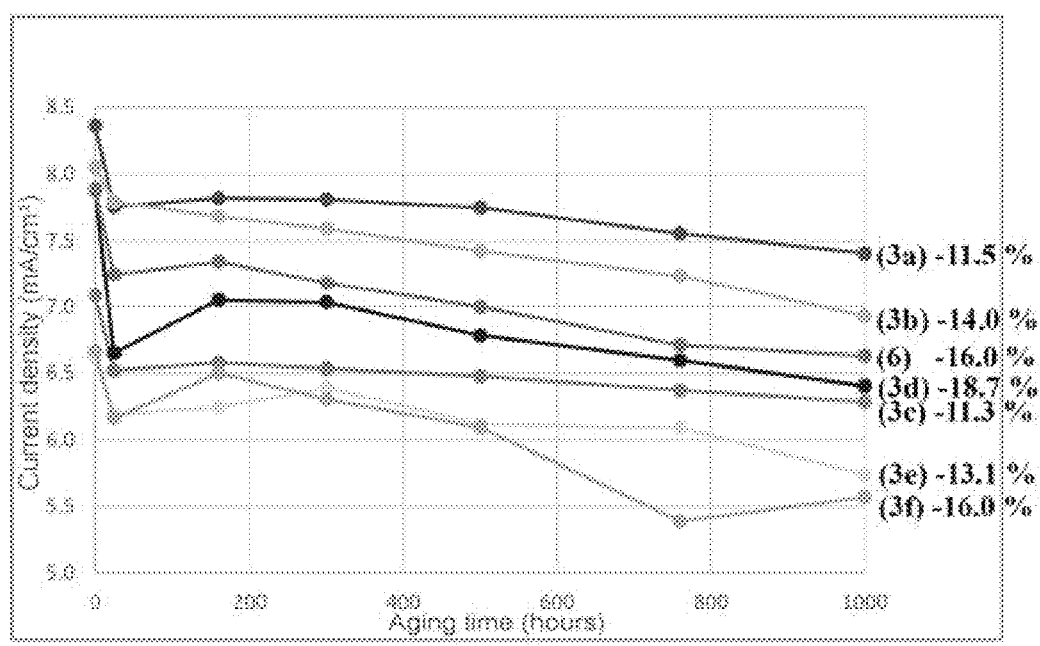
FIG. 7 is graph of the results in which the current density (in mA/cm$^2$) is a function of the aging time (in hours) from example 10.

The cells thus prepared were tested under conditions of accelerated aging at 60° C. under 100 mW·cm$^{-2}$ of incident light filtered against UV radiation with a wavelength of less than 340 nm. The results obtained are given by the appended FIG. 7, in which the current density (in mA/cm$^2$) is a function of the aging time (in hours). These results show that, a priori, the compounds of the 3 series are always very stable under these aging conditions since, after aging for 1000 hours, the retention of the efficiency is between 81% for the hexyl chain (compound 3d) and 89% for the methyl chain (compound 3a) and the propyl chain (compound 3c). Furthermore, the results appear to indicate that the propyl chain is the most stable. The series shows that, the longer the alkyl chain, the greater its solubility in the medium under consideration. On the other hand, the results appear to indicate that the conversion efficiency varies as a function of the length of the chain. The lengthening of the ester chain also slightly decreases the conversion efficiency but does not affect the stability, which remains noteworthy, much better than that of the state of the art (PC2). The compounds of the 3 series also show just as good a stability at low temperature of −40° C., analogous to the results obtained in the preceding example.

The invention claimed is:
1. An electrolyte composition comprising an electrolyte salt of following formula (I):

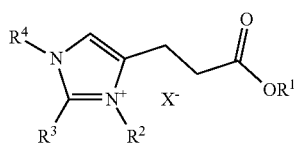

in which:
R$^1$ represents a hydrogen atom or a linear alkyl radical having from 1 to 10 carbon atoms;
R$^2$ and R$^4$, which are identical or different, each represent a linear or branched alkyl radical having from 1 to 15 carbon atoms, said alkyl radical optionally being substituted by one or more C$_6$-C$_{20}$ aryl groups which can optionally comprise one or more heteroatoms chosen from oxygen, sulfur and nitrogen atoms;
R$^3$ represents a hydrogen atom or a linear or branched alkyl radical having from 1 to 15 carbon atoms,
X$^-$ represents an iodide or bromide anion,
wherein said electrolyte salt is configured to be included in an electrolyte composition of a photoelectrochemical cell based on the sensitization to light of photoactive molecules,
and one or more additives intended to improve the performance of the photoelectrochemical cell chosen from benzimidazole derivatives; pyridine derivatives; triazole derivatives; pyrazole derivatives; imidazole derivatives; guanidine thiocyanate; chenodeoxycholic acid; magnesium iodide; and alkali metal salts of formula LiY or NaY in which Y is an I$^-$, Br$^-$, trifluorosulfonate, ClO$_4^-$, NO$_3^-$ or TFSI$^-$ anion.

2. The electrolyte composition as claimed in claim 1, wherein the photoelectrochemical cell based on sensitization to light of photoactive molecules is a dye-sensitized photovoltaic cell.

3. The electrolyte composition as claimed in claim 1, wherein the compounds of formula (I) are chosen from the group consisting of:
4-(3-methoxy-3-oxopropyl)-1,3-dimethyl-1H-imidazol-3-ium iodide,
4-(3-ethoxy-3-oxopropyl)-1,3-dimethyl-1H-imidazol-3-ium iodide,
4-(3-methoxy-3-oxopropyl)-1,3-diethyl-1H-imidazol-3-ium iodide,
4-(3-methoxy-3-oxopropyl)-1,3-dipropyl-1H-imidazol-3-ium iodide,
4-(3-methoxy-3-oxopropyl)-1,3-dibutyl-1H-imidazol-3-ium iodide,
4-(3-methoxy-3-oxopropyl)-1,3-dipentyl-1H-imidazol-3-ium iodide,
4-(3-methoxy-3-oxopropyl)-1,3-dihexyl-1H-imidazol-3-ium iodide,
4-(3-methoxy-3-oxopropyl)-1-methyl-3-propyl-1H-imidazol-3-ium iodide,
3-ethyl-4-(3-methoxy-3-oxopropyl)-1-methyl-1H-imidazol-3-ium iodide,
4-(3-methoxy-3-oxopropyl)-1-methyl-3-propyl-1H-imidazol-3-ium iodide,
3-butyl-4-(3-methoxy-3-oxopropyl)-1-methyl-1H-imidazol-3-ium iodide,
4-(3-methoxy-3-oxopropyl)-1-methyl-3-pentyl-1H-imidazol-3-ium iodide,
3-hexyl-4-(3-methoxy-3-oxopropyl)-1-methyl-1H-imidazol-3-ium iodide,
1-ethyl-4-(3-methoxy-3-oxopropyl)-3-methyl-1H-imidazol-3-ium iodide,
1,3-diethyl-4-(3-methoxy-3-oxopropyl)-1H-imidazol-3-ium iodide,
1-ethyl-4-(3-methoxy-3-oxopropyl)-3-propyl-1H-imidazol-3-ium iodide,
3-butyl-1-ethyl-4-(3-methoxy-3-oxopropyl)-1H-imidazol-3-ium iodide,
1-ethyl-4-(3-methoxy-3-oxopropyl)-3-pentyl-1H-imidazol-3-ium iodide,
1-ethyl-3-hexyl-4-(3-methoxy-3-oxopropyl)-1H-imidazol-3-ium iodide,
4-(3-methoxy-3-oxopropyl)-3-methyl-1-propyl-1H-imidazol-3-ium iodide,
3-ethyl-4-(3-methoxy-3-oxopropyl)-1-propyl-1H-imidazol-3-ium iodide,
4-(3-methoxy-3-oxopropyl)-1,3-dipropyl-1H-imidazol-3-ium iodide,
3-butyl-4-(3-methoxy-3-oxopropyl)-1-propyl-1H-imidazol-3-ium iodide, 4-(3-methoxy-3-oxopropyl)-3-pentyl-1-propyl-1H-imidazol-3-ium iodide,
3-hexyl-4-(3-methoxy-3-oxopropyl)-1-propyl-1H-imidazol-3-ium iodide,
1-butyl-4-(3-methoxy-3-oxopropyl)-3-methyl-1H-imidazol-3-ium iodide,
1-butyl-3-ethyl-4-(3-methoxy-3-oxopropyl)-1H-imidazol-3-ium iodide,
1-butyl-4-(3-methoxy-3-oxopropyl)-3-propyl-1H-imidazol-3-ium iodide,
1,3-dibutyl-4-(3-methoxy-3-oxopropyl)-1H-imidazol-3-ium iodide,
1-butyl-4-(3-methoxy-3-oxopropyl)-3-pentyl-1H-imidazol-3-ium iodide,
1-butyl-3-hexyl-4-(3-methoxy-3-oxopropyl)-1H-imidazol-3-ium iodide,
4-(3-methoxy-3-oxopropyl)-3-methyl-1-pentyl-1H-imidazol-3-ium iodide,
3-ethyl-4-(3-methoxy-3-oxopropyl)-1-pentyl-1H-imidazol-3-ium iodide,
4-(3-methoxy-3-oxopropyl)-1-pentyl-3-propyl-1H-imidazol-3-ium iodide,
3-butyl-4-(3-methoxy-3-oxopropyl)-1-pentyl-1H-imidazol-3-ium iodide,
4-(3-methoxy-3-oxopropyl)-1,3-dipentyl-1H-imidazol-3-ium iodide,
3-hexyl-4-(3-methoxy-3-oxopropyl)-1-pentyl-1H-imidazol-3-ium iodide,
1-hexyl-4-(3-methoxy-3-oxopropyl)-3-methyl-1H-imidazol-3-ium iodide,
3-ethyl-1-hexyl-4-(3-methoxy-3-oxopropyl)-1H-imidazol-3-ium iodide,
1-hexyl-4-(3-methoxy-3-oxopropyl)-3-propyl-1H-imidazol-3-ium iodide,
3-butyl-1-hexyl-4-(3-methoxy-3-oxopropyl)-1H-imidazol-3-ium iodide,
1-hexyl-4-(3-methoxy-3-oxopropyl)-3-pentyl-1H-imidazol-3-ium iodide,
1,3-dihexyl-4-(3-methoxy-3-oxopropyl)-1H-imidazol-3-ium iodide,
3-ethyl-4-(3-methoxy-3-oxopropyl)-1-methyl-1H-imidazol-3-ium bromide,
4-(3-methoxy-3-oxopropyl)-1-methyl-3-propyl-1H-imidazol-3-ium bromide,
3-butyl-4-(3-methoxy-3-oxopropyl)-1-methyl-1H-imidazol-3-ium bromide,
4-(3-methoxy-3-oxopropyl)-1-methyl-3-pentyl-1H-imidazol-3-ium bromide,
3-hexyl-4-(3-methoxy-3-oxopropyl)-1-methyl-1H-imidazol-3-ium bromide,
1-ethyl-4-(3-methoxy-3-oxopropyl)-3-methyl-1H-imidazol-3-ium bromide,
1,3-diethyl-4-(3-methoxy-3-oxopropyl)-1H-imidazol-3-ium bromide,
1-ethyl-4-(3-methoxy-3-oxopropyl)-3-propyl-1H-imidazol-3-ium bromide,
3-butyl-1-ethyl-4-(3-methoxy-3-oxopropyl)-1H-imidazol-3-ium bromide,
1-ethyl-4-(3-methoxy-3-oxopropyl)-3-pentyl-1H-imidazol-3-ium bromide,
1-ethyl-hexyl-4-(3-methoxy-3-oxopropyl)-1H-imidazol-3-ium bromide,
4-(3-methoxy-3-oxopropyl)-3-methyl-1-propyl-1H-imidazol-3-ium bromide,
3-ethyl-4-(3-methoxy-3-oxopropyl)-1-propyl-1H-imidazol-3-ium bromide,
4-(3-methoxy-3-oxopropyl)-1,3-dipropyl-1H-imidazol-3-ium bromide,
3-butyl-4-(3-methoxy-3-oxopropyl)-1-propyl-1H-imidazol-3-ium bromide,
4-(3-methoxy-3-oxopropyl)-3-pentyl-1-propyl-1H-imidazol-3-ium bromide,
3-hexyl-4-(3-methoxy-3-oxopropyl)-1-propyl-1H-imidazol-3-ium bromide,
1-butyl-4-(3-methoxy-3-oxopropyl)-3-methyl-1H-imidazol-3-ium bromide,
1-butyl-3-ethyl-4-(3-methoxy-3-oxopropyl)-1H-imidazol-3-ium bromide,
1-butyl-4-(3-methoxy-3-oxopropyl)-3-propyl-1H-imidazol-3-ium bromide,
1,3-dibutyl-4-(3-methoxy-3-oxopropyl)-1H-imidazol-3-ium bromide,
1-butyl-4-(3-methoxy-3-oxopropyl)-3-pentyl-1H-imidazol-3-ium bromide,
1-butyl-3-hexyl-4-(3-methoxy-3-oxopropyl)-1H-imidazol-3-ium bromide,
4-(3-methoxy-3-oxopropyl)-3-methyl-1-pentyl-1H-imidazol-3-ium bromide,
3-ethyl-4-(3-methoxy-3-oxopropyl)-1-pentyl-1H-imidazol-3-ium bromide,
4-(3-methoxy-3-oxopropyl)-1-pentyl-3-propyl-1H-imidazol-3-ium bromide,
3-butyl-4-(3-methoxy-3-oxopropyl)-1-pentyl-1H-imidazol-3-ium bromide,
4-(3-methoxy-3-oxopropyl)-1,3-dipentyl-1H-imidazol-3-ium bromide,
3-hexyl-4-(3-methoxy-3-oxopropyl)-1-pentyl-1H-imidazol-3-ium bromide,
1-hexyl-4-(3-methoxy-3-oxopropyl)-3-methyl-1H-imidazol-3-ium bromide,
3-ethyl-1-hexyl-4-(3-methoxy-3-oxopropyl)-1H-imidazol-3-ium bromide,
1-hexyl-4-(3-methoxy-3-oxopropyl)-3-propyl-1H-imidazol-3-ium bromide,
3-butyl-1-hexyl-4-(3-methoxy-3-oxopropyl)-1H-imidazol-3-ium bromide,
1-hexyl-4-(3-methoxy-3-oxopropyl)-3-pentyl-1H-imidazol-3-ium bromide,
1,3-dihexyl-4-(3-methoxy-3-oxopropyl)-1H-imidazol-3-ium bromide,
4-(3-methoxy-3-oxopropyl)-1,2,3-trimethyl-1H-imidazol-3-ium iodide,
3-ethyl-4-(3-methoxy-3-oxopropyl)-1,2-dimethyl-1H-imidazol-3-ium iodide,
4-(3-methoxy-3-oxopropyl)-1,2-dimethyl-3-propyl-1H-imidazol-3-ium iodide,
3-butyl-4-(3-methoxy-3-oxopropyl)-1,2-dimethyl-1H-imidazol-3-ium iodide,
4-(3-methoxy-3-oxopropyl)-1,2-dimethyl-3-pentyl-1H-imidazol-3-ium iodide,
3-hexyl-4-(3-methoxy-3-oxopropyl)-1,2-dimethyl-1H-imidazol-3-ium iodide,
1,3-diethyl-4-(3-methoxy-3-oxopropyl)-2-methyl-1H-imidazol-3-ium iodide,
4-(3-methoxy-3-oxopropyl)-2-methyl-1,3-dipropyl-1H-imidazol-3-ium iodide,
1,3-dibutyl-4-(3-methoxy-3-oxopropyl)-2-methyl-1H-imidazol-3-ium iodide,
4-(3-methoxy-3-oxopropyl)-2-methyl-1,3-dipentyl-1H-imidazol-3-ium iodide,
1,3-dihexyl-4-(3-methoxy-3-oxopropyl)-2-methyl-1H-imidazol-3-ium iodide, 1-ethyl-3-hexyl-4-(3-methoxy-3-oxopropyl)-2-methyl-1H-imidazol-3-ium iodide,
4-(3-methoxy-3-oxopropyl)-1-methyl-3-propyl-1H-imidazol-3-ium bromide,
4-(3-methoxy-3-oxopropyl)-1,2,3-trimethyl-1H-imidazol-3-ium bromide,
3-ethyl-4-(3-methoxy-3-oxopropyl)-1,2-dimethyl-1H-imidazol-3-ium bromide,
4-(3-methoxy-3-oxopropyl)-1,2-dimethyl-3-propyl-1H-imidazol-3-ium bromide,
3-butyl-4-(3-methoxy-3-oxopropyl)-1,2-dimethyl-1H-imidazol-3-ium bromide,
4-(3-methoxy-3-oxopropyl)-1,2-dimethyl-3-pentyl-1H-imidazol-3-ium bromide,
3-hexyl-4-(3-methoxy-3-oxopropyl)-1,2-dimethyl-1H-imidazol-3-ium bromide,
1,3-diethyl-4-(3-methoxy-3-oxopropyl)-2-methyl-1H-imidazol-3-ium bromide,
4-(3-methoxy-3-oxopropyl)-2-methyl-1,3-dipropyl-1H-imidazol-3-ium bromide,
1,3-dibutyl-4-(3-methoxy-3-oxopropyl)-2-methyl-1H-imidazol-3-ium bromide,
4-(3-methoxy-3-oxopropyl)-2-methyl-1,3-dipentyl-1H-imidazol-3-ium bromide, and
1-ethyl-3-hexyl-4-(3-methoxy-3-oxopropyl)-2-methyl-1H-imidazol-3-ium iodide.

4. A photoelectrochemical cell based on the sensitization to light of photoactive molecules comprising:
an assembly forming a photoelectrode comprising:
i) a transparent substrate coated with a layer of a transparent and conducting electrode material,
ii) a photoactive layer formed on said electrode material, said photoactive layer comprising a transparent carrier material and at least one photoactive molecule;
an assembly forming a counterelectrode; and
an electrolyte composition interposed between said photoactive layer and said counterelectrode, said electrolyte composition comprises, in an electrolyte solvent, a reversible redox pair ($I_3^-/I^-$) based on molecular iodine and on at least one compound of formula (I)

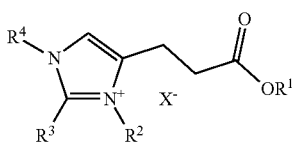

(I)

in which:
$R^1$ represents a hydrogen atom or a linear alkyl radical having from 1 to 10 carbon atoms;
$R^2$ and $R^4$, which are identical or different, each represent a linear or branched alkyl radical having from 1 to 15 carbon atoms, said alkyl radical optionally being substituted by one or more $C_6$-$C_{20}$ aryl groups which can optionally comprise one or more heteroatoms chosen from oxygen, sulfur and nitrogen atoms;
$R^3$ represents a hydrogen atom or a linear or branched alkyl radical having from 1 to 15 carbon atoms, and
$X^-$ represents an iodide or bromide anion.

5. The cell as claimed in claim 4, wherein said cell is a dye-sensitized photovoltaic cell.

6. The cell as claimed in claim 4, wherein the concentration of the compound or compounds of formula (I) within the electrolyte composition varies from 0.1 to 5 mol/l.

7. The cell as claimed in claim 4, wherein the concentration of molecular iodine within the electrolyte composition preferably varies from 0.001 to 0.5 mol/l.

8. The cell as claimed in claim 4, wherein the electrolyte solvent or solvents can be chosen from the group consisting of nitriles; sulfolane; dimethyl sulfoxide; dioxane; tetrahydrofuran; nitromethane; amides; N-methyl-2-pyrrolidinone; carbonates; ethylene glycols; alcohols, ketones; anhydrides; ethers; water; phthalates; adipates; citrates; sebacates; maleates; benzoates and succinates.

9. The cell as claimed in claim 4, wherein the solvent or solvents is an ionic liquid chosen from the group consisting of 1-ethyl-3-methylimidazolium bis(trifluoromethanesulfonyl)imide, 1-butyl-3-methylimidazolium bis(trifluoromethanesulfonyl)imide, 1-butyl-3-methylimidazolium hexafluorophosphate, 1-butyl-1-methylpyrrolidinium bis(trifluoromethylsulfonyl)imide and their mixtures.

10. The cell as claimed in claim 4, wherein the electrolyte composition additionally includes one or more additives chosen from the group consisting of benzimidazole derivatives; pyridine derivatives; triazole derivatives; pyrazole derivatives; imidazole derivatives; ethylene carbonate; guanidine thiocyanate and chenodeoxycholic acid; magnesium iodide; and alkali metal salts of formula LiY or NaY in which Y is an $I^-$, $Br^-$, trifluorosulfonate, $ClO_4^-$, $NO_3^-$ or $TFSI^-$ anion.

11. The cell as claimed in claim 4, wherein the transparent substrate of the photoelectrode is made of a flexible or rigid material chosen from glass or a sheet made of a plastic material.

12. The cell as claimed in claim 4, wherein the electrode material of the photoelectrode is applied to the transparent substrate and is provided in the form of a layer of a transparent conducting oxide chosen from the group consisting of tin oxide doped with fluorine, indium tin oxide, indium oxide doped with antimony and zinc oxide doped with aluminum, with gallium or with indium.

13. The cell as claimed in claim 4, wherein the photoactive molecule of the photoactive layer is a ruthenium or osmium complex.

14. The cell as claimed in claim 4, wherein the counterelectrode is made of a transparent counter substrate coated with a layer of $SnO_2$:F or of doped ZnO or with a stack of transparent conducting layers and in that a layer of catalyst is formed on the material forming counterelectrode.

15. The cell as claimed in claim 14, wherein the layer of catalyst is a layer of platinum or of carbon or of inorganic chalcogenide.

16. A compound of the following formula (I'):

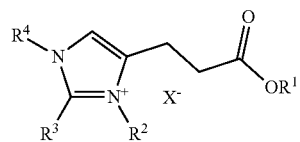

(I')

in which:
$R^1$ represents a hydrogen atom or a linear alkyl radical having from 1 to 10 carbon atoms,
$R^2$ and $R^4$, which are identical or different, each represent a linear or branched alkyl radical having from 1 to 15 carbon atoms, said alkyl radical optionally being substituted by one or more $C_6$-$C_{20}$ aryl groups which can optionally comprise one or more heteroatoms chosen from oxygen, sulfur and nitrogen atoms, $R^3$ represents a hydrogen atom or a linear or branched alkyl radical having from 1 to 15 carbon atoms, $X^-$ represents an iodide or bromide anion, wherein:
when $X^-$ represents an iodide anion, when $R^1$ represents a methyl radical and when $R^3$ is a hydrogen atom, then the $R^2$ and $R^4$ radicals cannot simultaneously represent a methyl radical or an ethyl radical, when $X^-$ represents a bromide anion, when $R^1$ represents a methyl radical and when $R^3$ is a hydrogen atom, then the $R^2$ and $R^4$ radicals cannot simultaneously represent a benzyl radical, when $X^-$ represents a bromide anion, when $R^1$ represents a methyl radical, when $R^2$ is a butyl radical and when $R^3$ is a hydrogen atom, then the $R^4$ radical is other than a methyl, ethyl or benzyl radical, when $X^-$ represents an iodide anion, when $R^1$ and $R^2$ represent a methyl radical and when $R^3$ is a hydrogen atom, then the $R^4$ radical is other than a trityl radical, and when $X^-$ represents a bromide anion, when $R^1$ represents a methyl radical, when $R^2$ is a butyl radical and when $R^3$ is an isopropyl radical, then the $R^4$ radical is other than a methyl radical.

17. The compound of formula (I') as claimed in claim 16, wherein said compound of formula (I') is chosen from:
- 4-(3-ethoxy-3-oxopropyl)-1,3-dimethyl-1H-imidazol-3-ium iodide,
- 4-(3-methoxy-3-oxopropyl)-1,3-dipropyl-1H-imidazol-3-ium iodide,
- 4-(3-methoxy-3-oxopropyl)-1,3-dibutyl-1H-imidazol-3-ium iodide,
- 4-(3-methoxy-3-oxopropyl)-1,3-dipentyl-1H-imidazol-3-ium iodide,
- 4-(3-methoxy-3-oxopropyl)-1,3-dihexyl-1H-imidazol-3-ium iodide,
- 3-ethyl-4-(3-methoxy-3-oxopropyl)-1-methyl-1H-imidazol-3-ium iodide,
- 4-(3-methoxy-3-oxopropyl)-1-methyl-3-propyl-1H-imidazol-3-ium iodide,
- 3-butyl-4-(3-methoxy-3-oxopropyl)-1-methyl-1H-imidazol-3-ium iodide,
- 4-(3-methoxy-3-oxopropyl)-1-methyl-3-pentyl-1H-imidazol-3-ium iodide,
- 3-hexyl-4-(3-methoxy-3-oxopropyl)-1-methyl-1H-imidazol-3-ium iodide,
- 1-ethyl-4-(3-methoxy-3-oxopropyl)-3-methyl-1H-imidazol-3-ium iodide,
- 1-ethyl-4-(3-methoxy-3-oxopropyl)-3-propyl-1H-imidazol-3-ium iodide,
- 3-butyl-1-ethyl-4-(3-methoxy-3-oxopropyl)-1H-imidazol-3-ium iodide,
- 1-ethyl-4-(3-methoxy-3-oxopropyl)-3-pentyl-1H-imidazol-3-ium iodide,
- 1-ethyl-3-hexyl-4-(3-methoxy-3-oxopropyl)-1H-imidazol-3-ium iodide,
- 4-(3-methoxy-3-oxopropyl)-3-methyl-1-propyl-1H-imidazol-3-ium iodide,
- 3-ethyl-4-(3-methoxy-3-oxopropyl)-1-propyl-1H-imidazol-3-ium iodide,
- 4-(3-methoxy-3-oxopropyl)-1,3-dipropyl-1H-imidazol-3-ium iodide,
- 3-butyl-4-(3-methoxy-3-oxopropyl)-1-propyl-1H-imidazol-3-ium iodide,
- 4-(3-methoxy-3-oxopropyl)-3-pentyl-1-propyl-1H-imidazol-3-ium iodide,
- 3-hexyl-4-(3-methoxy-3-oxopropyl)-1-propyl-1H-imidazol-3-ium iodide,
- 1-butyl-4-(3-methoxy-3-oxopropyl)-3-methyl-1H-imidazol-3-ium iodide,
- 1-butyl-3-ethyl-4-(3-methoxy-3-oxopropyl)-1H-imidazol-3-ium iodide,
- 1-butyl-4-(3-methoxy-3-oxopropyl)-3-propyl-1H-imidazol-3-ium iodide,
- 1,3-dibutyl-4-(3-methoxy-3-oxopropyl)-1H-imidazol-3-ium iodide,
- 1-butyl-4-(3-methoxy-3-oxopropyl)-3-pentyl-1H-imidazol-3-ium iodide,
- 1-butyl-3-hexyl-4-(3-methoxy-3-oxopropyl)-1H-imidazol-3-ium iodide,
- 4-(3-methoxy-3-oxopropyl)-3-methyl-1-pentyl-1H-imidazol-3-ium iodide,
- 3-ethyl-4-(3-methoxy-3-oxopropyl)-1-pentyl-1H-imidazol-3-ium iodide,
- 4-(3-methoxy-3-oxopropyl)-1-pentyl-3-propyl-1H-imidazol-3-ium iodide,
- 3-butyl-4-(3-methoxy-3-oxopropyl)-1-pentyl-1H-imidazol-3-ium iodide,
- 4-(3-methoxy-3-oxopropyl)-1,3-dipentyl-1H-imidazol-3-ium iodide,
- 3-hexyl-4-(3-methoxy-3-oxopropyl)-1-pentyl-1H-imidazol-3-ium iodide,
- 1-hexyl-4-(3-methoxy-3-oxopropyl)-3-methyl-1H-imidazol-3-ium iodide,
- 3-ethyl-1-hexyl-4-(3-methoxy-3-oxopropyl)-1H-imidazol-3-ium iodide,
- 1-hexyl-4-(3-methoxy-3-oxopropyl)-3-propyl-1H-imidazol-3-ium iodide,
- 3-butyl-1-hexyl-4-(3-methoxy-3-oxopropyl)-1H-imidazol-3-ium iodide,
- 1-hexyl-4-(3-methoxy-3-oxopropyl)-3-pentyl-1H-imidazol-3-ium iodide,
- 1,3-dihexyl-4-(3-methoxy-3-oxopropyl)-1H-imidazol-3-ium iodide,
- 3-ethyl-4-(3-methoxy-3-oxopropyl)-1-methyl-1H-imidazol-3-ium bromide,
- 4-(3-methoxy-3-oxopropyl)-1-methyl-3-propyl-1H-imidazol-3-ium bromide,
- 4-(3-methoxy-3-oxopropyl)-1-methyl-3-pentyl-1H-imidazol-3-ium bromide,
- 3-hexyl-4-(3-methoxy-3-oxopropyl)-1-methyl-1H-imidazol-3-ium bromide,
- 1-ethyl-4-(3-methoxy-3-oxopropyl)-3-methyl-1H-imidazol-3-ium bromide,
- 1,3-diethyl-4-(3-methoxy-3-oxopropyl)-1H-imidazol-3-ium bromide,
- 1-ethyl-4-(3-methoxy-3-oxopropyl)-3-propyl-1H-imidazol-3-ium bromide,
- 1-ethyl-4-(3-methoxy-3-oxopropyl)-3-pentyl-1H-imidazol-3-ium bromide,
- 1-ethyl-3-hexyl-4-(3-methoxy-3-oxopropyl)-1H-imidazol-3-ium bromide,
- 4-(3-methoxy-3-oxopropyl)-3-methyl-1-propyl-1H-imidazol-3-ium bromide,
- 3-ethyl-4-(3-methoxy-3-oxopropyl)-1-propyl-1H-imidazol-3-ium bromide,
- 4-(3-methoxy-3-oxopropyl)-1,3-dipropyl-1H-imidazol-3-ium bromide,
- 3-butyl-4-(3-methoxy-3-oxopropyl)-1-propyl-1H-imidazol-3-ium bromide, 4-(3-methoxy-3-oxopropyl)-3-pentyl-1-propyl-1H-imidazol-3-ium bromide,
3-hexyl-4-(3-methoxy-3-oxopropyl)-1-propyl-1H-imidazol-3-ium bromide,
1-butyl-4-(3-methoxy-3-oxopropyl)-3-propyl-1H-imidazol-3-ium bromide,
1,3-dibutyl-4-(3-methoxy-3-oxopropyl)-1H-imidazol-3-ium bromide,
1-butyl-4-(3-methoxy-3-oxopropyl)-3-pentyl-1H-imidazol-3-ium bromide,
1-butyl-3-hexyl-4-(3-methoxy-3-oxopropyl)-1H-imidazol-3-ium bromide,
4-(3-methoxy-3-oxopropyl)-3-methyl-1-pentyl-1H-imidazol-3-ium bromide,
3-ethyl-4-(3-methoxy-3-oxopropyl)-1-pentyl-1H-imidazol-3-ium bromide,
4-(3-methoxy-3-oxopropyl)-1-pentyl-3-propyl-1H-imidazol-3-ium bromide,
3-butyl-4-(3-methoxy-3-oxopropyl)-1-pentyl-1H-imidazol-3-ium bromide,
4-(3-methoxy-3-oxopropyl)-1,3-dipentyl-1H-imidazol-3-ium bromide,
3-hexyl-4-(3-methoxy-3-oxopropyl)-1-pentyl-1H-imidazol-3-ium bromide,
1-hexyl-4-(3-methoxy-3-oxopropyl)-3-methyl-1H-imidazol-3-ium bromide,
3-ethyl-1-hexyl-4-(3-methoxy-3-oxopropyl)-1H-imidazol-3-ium bromide,
1-hexyl-4-(3-methoxy-3-oxopropyl)-3-propyl-1H-imidazol-3-ium bromide,
3-butyl-1-hexyl-4-(3-methoxy-3-oxopropyl)-1H-imidazol-3-ium bromide,
1-hexyl-4-(3-methoxy-3-oxopropyl)-3-pentyl-1H-imidazol-3-ium bromide,
1,3-dihexyl-4-(3-methoxy-3-oxopropyl)-1H-imidazol-3-ium bromide,
4-(3-methoxy-3-oxopropyl)-1,2,3-trimethyl-1H-imidazol-3-ium iodide,
3-ethyl-4-(3-methoxy-3-oxopropyl)-1,2-dimethyl-1H-imidazol-3-ium iodide,
4-(3-methoxy-3-oxopropyl)-1,2-dimethyl-3-propyl-1H-imidazol-3-ium iodide,
3-butyl-4-(3-methoxy-3-oxopropyl)-1,2-dimethyl-1H-imidazol-3-ium iodide,
4-(3-methoxy-3-oxopropyl)-1,2-dimethyl-3-pentyl-1H-imidazol-3-ium iodide,
3-hexyl-4-(3-methoxy-3-oxopropyl)-1,2-dimethyl-1H-imidazol-3-ium iodide,
1,3-diethyl-4-(3-methoxy-3-oxopropyl)-2-methyl-1H-imidazol-3-ium iodide,
4-(3-methoxy-3-oxopropyl)-2-methyl-1,3-dipropyl-1H-imidazol-3-ium iodide,
1,3-dibutyl-4-(3-methoxy-3-oxopropyl)-2-methyl-1H-imidazol-3-ium iodide,
4-(3-methoxy-3-oxopropyl)-2-methyl-1,3-dipentyl-1H-imidazol-3-ium iodide,
1,3-dihexyl-4-(3-methoxy-3-oxopropyl)-2-methyl-1H-imidazol-3-ium iodide,
1-ethyl-3-hexyl-4-(3-methoxy-3-oxopropyl)-2-methyl-1H-imidazol-3-ium iodide,
4-(3-methoxy-3-oxopropyl)-1-methyl-3-propyl-1H-imidazol-3-ium bromide,
4-(3-methoxy-3-oxopropyl)-1,2,3-trimethyl-1H-imidazol-3-ium bromide,
3-ethyl-4-(3-methoxy-3-oxopropyl)-1,2-dimethyl-1H-imidazol-3-ium bromide,
4-(3-methoxy-3-oxopropyl)-1,2-dimethyl-3-propyl-1H-imidazol-3-ium bromide,
3-butyl-4-(3-methoxy-3-oxopropyl)-1,2-dimethyl-1H-imidazol-3-ium bromide,
4-(3-methoxy-3-oxopropyl)-1,2-dimethyl-3-pentyl-1H-imidazol-3-ium bromide,
3-hexyl-4-(3-methoxy-3-oxopropyl)-1,2-dimethyl-1H-imidazol-3-ium bromide,
1,3-diethyl-4-(3-methoxy-3-oxopropyl)-2-methyl-1H-imidazol-3-ium bromide,
4-(3-methoxy-3-oxopropyl)-2-methyl-1,3-dipropyl-1H-imidazol-3-ium bromide,
1,3-dibutyl-4-(3-methoxy-3-oxopropyl)-2-methyl-1H-imidazol-3-ium bromide,
4-(3-methoxy-3-oxopropyl)-2-methyl-1,3-dipentyl-1H-imidazol-3-ium bromide, and
1-ethyl-3-hexyl-4-(3-methoxy-3-oxopropyl)-2-methyl-1H-imidazol-3-ium iodide.

* * * * *